United States Patent [19]

Cooke et al.

[11] Patent Number: 4,738,959
[45] Date of Patent: * Apr. 19, 1988

[54] ANTIBACTERIAL PENEM DERIVATIVES

[75] Inventors: Michael D. Cooke, Newport Pagnell; Barry C. Ross, Luton, both of United Kingdom

[73] Assignee: Hoechst UK Limited, United Kingdom

[*] Notice: The portion of the term of this patent subsequent to Apr. 29, 2003 has been disclaimed.

[21] Appl. No.: 511,284

[22] Filed: Jul. 6, 1983

[30] Foreign Application Priority Data

Jul. 8, 1982 [GB] United Kingdom ............... 8219745

[51] Int. Cl.$^4$ ................. C07D 499/00; A61K 31/425
[52] U.S. Cl. .................... 514/19 S; 540/310; 514/192
[58] Field of Search ............ 260/245.2 T, 245.2 R; 514/192, 19 S; 540/310

[56] References Cited

U.S. PATENT DOCUMENTS

| 4,301,074 | 11/1981 | Christensen et al. | 260/245.2 R |
|---|---|---|---|
| 4,395,418 | 7/1983 | Ohki et al. | 260/245.2 R |
| 4,431,658 | 2/1984 | Afonso et al. | 260/245.2 R |
| 4,585,767 | 4/1986 | Cooke et al. | 514/210 |

FOREIGN PATENT DOCUMENTS 56-115788 9/1981 Japan .
2104511 3/1983 United Kingdom .

Primary Examiner—Nicholas S. Rizzo
Attorney, Agent, or Firm—Finnegan, Henderson, Farabow, Garrett & Dunner

[57] ABSTRACT

The present invention relates to certain penem derivatives of the general formula I

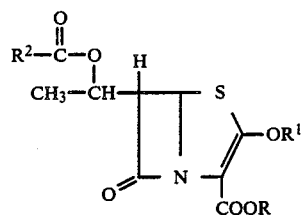

in which R represents a hydrogen atom or a carboxyl esterifying group, $R^1$ represents certain unsubstituted and substituted aromatic and heterocyclic groups, and $R^2$ represents a hydrogen atom, an unsubstituted or substituted alkyl or aryl group.

The compound of formula I and salts thereof may be used in the treatment of bacterial infections in man and other animals.

13 Claims, No Drawings

ANTIBACTERIAL PENEM DERIVATIVES

Certain penem derivatives possessing a substituted oxy group at the two-position and a 1'-hydroxyethyl group at the six-position are known from U.K. patent specification 2,102,798. These compounds have antibacterial and/or β-lactamase inhibitory properties. Some of these compounds are effective after oral administering. It has now been found that this highly desirable property can be enhanced through acylation of the 1'-hydroxy ethyl group.

Accordingly, the present invention relates to penem derivatives, to a process for their preparation, to pharmaceutical preparations comprising them, and to intermediates for use in the preparation of substances having antibacterial activity and/or β-lactamase inhibitory and/or inactivating activity.

The term "penem" is used herein to denote the following structure:

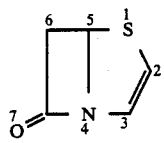

The present invention provides a compound of the general formula I

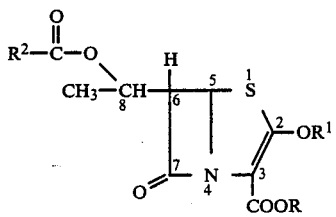

in which R represents a hydrogen atom or a carboxyl esterifying group, $R^1$ represents a phenyl, naphthyl, thienyl, pyridyl, quinolyl or isoquinolyl group bonded at a ring carbon atom to the oxygen atom attached to the 2-position of the penem ring structure, a group $R^1$ being unsubstituted or substituted by one, two or three substituents, which may be the same or different, selected from halogen atoms and —OH, —NH$_2$, —NO$_2$, —CN, —N$_3$, $R^3$—, $R^3$O—, $R^3$S—, $R^3$—SO—, $R^3$—SO$_2$—, $R^3$—CO—, $R^3$O—CO—, $R^3$—CO—O—, H$_2$N—CO—,

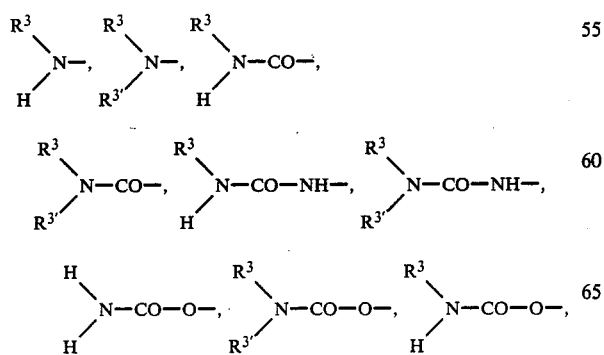

$R^3$—CO—NH—, NH$_2$—CO—NH—, $R^3$—SO$_2$—NH—, NH$_2$—SO$_2$—NH—, H$_2$N—SO$_2$—,

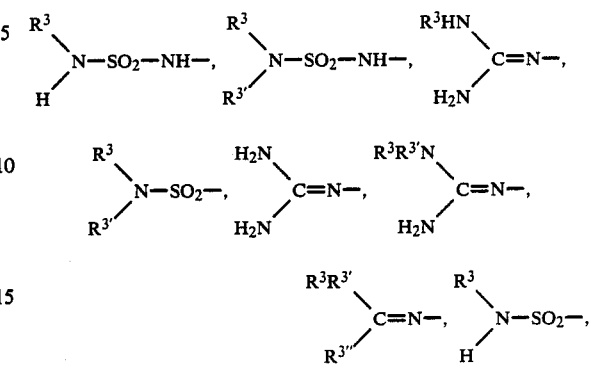

—CF$_3$, —SCF$_3$, —SOCF$_3$, —SO$_2$CF$_3$ and HO—CO—groups, in which $R^3$, $R^{3'}$ and $R^{3''}$ each represents an alkyl group having from 1 to 4 carbon atoms, $R^3$, $R^{3'}$ and $R^{3''}$ being the same or different, and $R^2$ represents
  (i) a hydrogen atom, or
  (ii) a straight or branched chain alkyl group having from 1 to 15, for example 1 to 9, preferably 1 to 7 and, especially 1 to 5 carbon atoms, and which is unsubstituted or is substituted by one or more substituents, which may be the same or different, selected from the following:
    (a) alkyl, alkenyl and alkynyl groups having up to 4 carbon atoms;
    (b) cycloalkyl and cycloalkenyl groups having from 3 to 7 carbon atoms;
    (c) aryl groups, which may be unsubstituted or substituted by one or more substituents, which may be the same or different, selected from alkyl, alkylthio and alkoxy groups having up to 4 carbon atoms; halogen atoms, trifluoromethyl groups; cyano groups; carboxyl groups; groups of the formula —COOR$^4$ in which $R^4$ represents an alkyl group having up to 4 carbon atoms; amido and sulphonamido groups; groups of the formula

which $R^5$ and $R^6$, which may be the same or different, each respresents a hydrogen atom or a group —COR$^4$, —SO$_2$R$^4$ or R$^4$, in which R$^4$ is defined as above;
    (d) trifluoromethyl and 2,2,2-trifluoroethyl groups;
    (e) halogen atoms,
    (f) free hydroxy groups and substituted, for example, protected hydroxy groups, for example, alkoxy groups having up to 4 carbon atoms and aryloxy groups in which the aryl moiety may be substituted as define in (c) above, acyloxy groups of the formula R$^2$CO$_2$— and acyl groups of the formula R$^2$CO—, in which R$^2$ is as defined above;
    (g) cyano and azido groups; and
    (h) amino groups and groups of the formula

in which $R^5$ and $R^6$ are as defined in (c) above; or $R^2$ represents a cycloalkyl group which may be unsubstituted or substituted as defined above for an alkyl group $R^2$; or $R^2$ represents an aryl group which may be unsubstituted or substituted as defined in (c) above; or (iii) $R^2$ represents a cycloalkyl group which may be unsubstituted or substituted as defined above for an alkyl group $R^2$; or (iv) $R^2$ represents an aryl group which may be unsubstituted or substituted as defined in (c) above.

The invention also provides salts of a compound of formula I, especially physiologically tolerable salts thereof.

The stereochemistry at positions 5, 6 and 8 can be R or S independently (R and S being as defined by the Cahn-Ingold-Prelog system of nomenclature). The preferred stereo-chemistry at position 5 is R, at position 6 is S, and at position 8 is R.

The present invention also provides a process for the production of a compound of the general formula I or a salt thereof, which comprises
reacting a compound of the general formula II

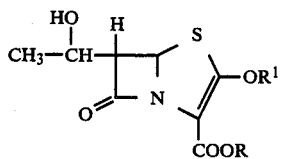

in which R and $R^1$ are as defined above, with an acylating agent comprising the group $R^2$, and, if desired, carrying out any one or more of the following steps in any desired order:

(a) converting an ester of formula I into the corresponding free acid,
(b) converting a free acid of formula I into an ester thereof,
(c) transesterifying a compound of formula I,
(d) converting a free acid or an ester of formula I into a salt, or a salt into the free acid, an ester, or another salt,
(e) removing any protective groups present other than an esterifying group R,
(f) converting a group $R^2$ into another group $R^2$,
(g) converting a substituent of a group $R^1$ into another substituent of $R^1$, and
(h) converting a substituent of a group $R^2$ into another substituent thereof.

The acylating agent comprising the group

is for example, an acylating agent of the formula $R^2COBr$, $R^2COCl$ or $(R^2CO)_2O$ in which $R^2$ is defined as above.

The acylation reaction is generally carried out in an inert, aprotic solvent, for example, tetrahydrofuran, toluene or methylene dichloride, and at a temperature within the range of from $-40°$ to $+70°$ C., preferably from $0°$ to $20°$ C.

The reaction is preferably carried out in the presence of a base, for example, an inorganic base, a tertiary amine or a heterocyclic base having a $pK_a \leq 15$, preferably from 5 to 9. Examples of bases are triethylamine, pyridine, substituted pyridines, for example, 4-dimethylaminopyridine, and imidazole. The amount of base used is generally 1 equivalent per equivalent of acylating agent. 4-Dimethylamino-pyridine may be present in a catalytic amount, in addition to another base.

The term "lower" as used herein denotes a molecule, group or radical having up to 4 carbon atoms. Unless stated otherwise, halogen atoms are fluorine, chlorine, bromine and iodine atoms. The term "known" means in actual use in the art or described in the literature of the art.

$R^1$ may represent, for example, an unsubstituted phenyl group or a phenyl group substituted by a chlorine, fluorine, trifluoromethyl, methyl, methoxy, nitro, cyano, amino, hydroxy, acetoxy, methylthio, methylsulphinyl, methylsulphonyl, methylcarbonylamino, methylsulphonylamino group, especially a hydroxy, acetoxy, cyano, methylsulphinyl or methylsulphonyl group. $R^1$ may also represent a phenyl group substituted by more than one group, for example, by two or three methyl or methoxy groups. A heterocyclic group $R^1$ may also carry up to three substituents, for example, one or two methyl groups, preferably at ring carbon atoms.

A group $R^1$, especially a phenyl or thienyl group, is preferably substituted by one, two or three substituents, which may be the same or different, selected from halogen atoms, especially fluorine atoms; cyano groups; and lower alkylsulphinyl and lower alkylsulphonyl groups, especially methylsulphinyl, ethylsulphinyl and methylsulphonyl groups. Preferably only one substituent is present.

It will be appreciated that the choice of substituents for $R^1$ may be subject to considerations of stereochemistry and also of possible interactions between the substituents themselves and other parts of a molecule in which $R^1$ is present, for example, $R^1$ may have 1, 2 or 3 substituents, but not more than one should be selected from (a) —OH and —NH$_2$ groups
and not more than one should be selected from
(b) —CN, —NO$_2$, $R^3$—CO—, $R^3$O—CO—, $R^3$—SO— and $R^3$—SO$_2$—groups. (Other substituents may, of course, be present on $R^1$ in addition to a group selected from (a) and/or a group selected from (b).)

The expert will be aware of any restrictions on the choice of substituents, as such restrictions are known in the art. $R^2$ preferably represents a hydrogen atom; an alkyl group having up to 5 carbon atoms, especially a methyl or pentyl group; a trifluoromethyl group; a $(C_1-C_4)$-alkoxy-$(C_1-C_5)$-alkyl group, preferably a methoxy-$(C_1-C_5)$-alkyl or ethoxy-$(C_1-C_5)$-alkyl group, and especially a methoxymethyl or ethoxymethyl group; a phenoxy-$(C_1-C_5)$-alkyl group, especially a phenoxymethyl group; a cycloalkyl group, especially a cyclopropyl group; a $(C_3-C_7)$-cycloalkyl-$(C_1-C_5)$-alkyl group, especially a cyclopentylmethyl group; an amino-$(C_1-C_5)$-alkyl group, especially an aminomethyl group; a phenyl group which may be substituted by one of the substituents defined above, especially a tolyl group or a chlorophenyl group, in particular a 4-chlorophenyl group or a benzyl group.

An esterified carboxyl group —COOR is, for example, an ester formed with an unsubstituted or substituted aliphatic, cycloaliphatic, cycloaliphatic-aliphatic, aryl, araliphatic, heterocyclic or heterocyclic-aliphatic alcohol having up to 20 carbon atoms or is, for example, a silyl or stannyl ester.

An aliphatic group R is, for example a straight or branched chain substituted or unsubstituted alkyl, alkenyl or alkynyl group having up to 18 carbon atoms, preferably up to 8 carbon atoms, and especially up to 4 carbon atoms, for example, a methyl, ethyl, n-propyl, iso-propyl, n-butyl, sec-butyl, isobutyl, tert-butyl, n-pentyl, n-hexyl, allyl, or vinyl group.

An aliphatic group R, especially a methyl group, may be substituted by a cycloalkyl, aryl or heterocyclic group, for example, a pyridylmethyl group, or R may itself represent a cycloalkyl, aryl or heterocyclic group.

A cycloaliphatic group R may have up to 18 carbon atoms and is, for example, a cyclopentyl, cyclohexyl or adamantyl group. An aryl group R may have up to 12 carbon atoms and may have two or more fused rings. An aryl group R is, for example, an unsubstituted or substituted phenyl group, and an unsubstituted or substituted aralkyl group is, for example, a benzyl, p-nitrobenzyl or benzhydryl group.

A heterocyclic group R may have one or more, preferably one to three, heteroatoms, which may be the same or different, selected from oxygen, nitrogen and sulphur, and up to 14 atoms in total. A heterocyclic group is, for example, an oxygen-containing heterocyclic group, for example, a tetrahydropyranyl or phthalidyl group.

A stannyl group R may have up to 24 carbon atoms, for example, R may represent a stannyl group having three substituents, which may be the same or different, selected from alkyl, alkenyl, cycloalkyl, aryl, aralkyl, alkoxy and aralkoxy groups, for example, alkyl groups having up to 4 carbon atoms, for example, n-butyl groups, phenyl and benzyl groups, especially three n-butyl groups.

A silyl group R has three substituents on the silicon atom and preferably up to 24 carbon atoms in total. The three substituents may be the same or difrerent, and selected from alkyl, alkenyl, cycloalkyl, aryl and aralkyl groups, preferably selected from alkyl groups having up to 4 carbon atoms and phenyl groups, especially selected from methyl, t-butyl and phenyl groups. Preferred silyl groups are trimethylsilyl, diphenyl-t-butylsilyl, and dimethyl-t-butylsilyl groups.

Any group R that is capable of substitution may be substituted. Examples of substituents are halogen atoms; HO—, $R^3O$—, $R^3$—CO—, $R^3O$—CO—, $R^3S$—CO—, $R^3$—CO—S—, $H_2N$—CO—, $H_2N$—CO—O—,

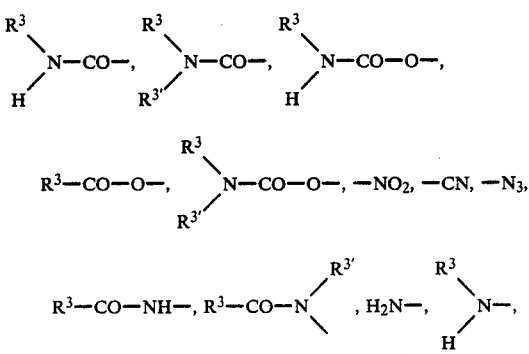

-continued

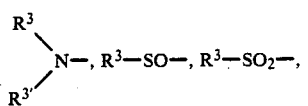

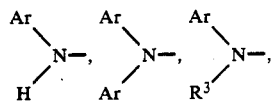

$R^3$—$SO_2$—NH—, Ar, ArO—, ArO—CO—, Ar—S—CO—, Ar—CO—O—, Ar—CO—S—, Ar—$R^3O$—CO—, Ar—$R^3S$—CO—, Ar—$R^3$—CO—O—, Ar—$R^3$—CO—S—, Ar—$R^3O$—, Ar—$R^3S$—, in which $R^3$ and $R^{3'}$ are as defined above, and Ar denotes an aryl group, especially a phenyl group; aromatic and non-aromatic heterocyclic groups, for example, having one or more heteroatoms, for example, up to 3 heteroatoms, which may be the same or different, selected from nitrogen, oxygen and sulphur atoms, and preferably up to 14 atoms in total, and the corresponding heterocyclicoxy groups and heterocyclicthio groups. When R represents other than an aliphatic group, a further possible substituent is a lower alkyl group.

The group R may be removable by hydrolysis, by photolysis, by reduction or by enzyme action to give the free acid, or two or more methods may be used, for example, reduction followed by hydrolysis. A group R that may be removed readily without substantial degradation of the rest of the molecule is particularly useful as a carboxyl protecting group. Examples of esters that are readily split by reduction are arylmethyl esters, for example, benzyl, p-nitrobenzyl, benzhydryl and trityl esters. Reduction of an ester, for example, an arylmethyl ester, may be carried out using hydrogen and a metal catalyst, for example, a noble metal, for example, platinum, palladium or rhodium, which catalyst may be supported, for example on charcoal or kieselguhr. Alternatively, a p-nitrobenzyl ester may be converted to the free acid by a two-step method, with an initial reduction of the nitro group, followed by hydrolysis. The nitro group may be reduced by noble metal catalysed hydrogenation, for example, using platinum, or palladium on carbon, or by a metal reducing agent, for example, zinc in acetic acid. Other metal reducing agents are, for example, aluminum amalgam, and iron and ammonium chloride, see, for example, British Patent Specification No. 1,582,960. Reduction of the nitro group is followed by hydrolysis which may occur in situ during reduction of the nitro group or which may be carried out subsequently by treatment with an acid or a base. An o-nitrobenzyl ester may be converted to the free acid by photolysis.

A stannyl ester, for example, a tri-n-butyl stannyl ester, may be split readily by hydrolysis, for example, by solvolysis, for example, using water, an alcohol, a phenol or a carboxylic acid, for example, acetic acid.

Certain ester groups may be split off by base hydrolysis, for example, acetylmethyl and acetoxymethyl ester groups. There may be used an esterifying group that is removable under physiological conditions, that is to say, the esterifying group is split off in vivo to give the free acid or the carboxylate, for example, an acyloxymethyl ester, e.g. an acetoxymethyl or pivaloyloxymethyl ester, an aminoalkanoyloxymethyl ester, for example, an L-glycyloxymethyl, L-valyloxymethyl or L-leucyloxymethyl ester, or a phthalidyl ester, or an optionally substituted 2-amino-ethyl ester, for example, a 2-diethylaminoethyl or 2-(1-morpholino)-ethyl ester.

Preferred esters are the p-nitrobenzyl, phthalidyl, pivaloyloxymethyl, acetylmethyl and acetoxymethyl esters.

An ester of formula I, or of any other free acid described herein, may be prepared by reaction with an alcohol, phenol or stannanol, or a reactive derivative thereof. The reaction is preferably carried out under mild conditions in order to prevent rupture of the ring or ring system, for example, under neutral or mild acidic or basic conditions, and at temperatures within the range of from $-70°$ to $+35°$ C.

An alkyl, alkoxyalkyl or aralkyl ester may be prepared by reaction of an acid of formula I or any other free acid with the appropriate diazoalkane or diazoaralkane for example, diazomethane or diphenyldiazomethane. The reaction is preferably carried out in an ether, ester or halogenohydrocarbon as solvent, for example, in diethyl ether, ethyl acetate or dichloromethane. In general, temperatures below room temperature are preferred, for example, from $-15°$ to $+15°$ C.

An ester derived from an alcohol may also be produced by reaction of a reactive derivative of the alcohol, for example, a halide, for example a chloride, bromide or iodide, or a hydrocarbonsulphonyl derivative, for example, a mesyl or tosyl ester, with a salt of an acid of formula I or another free acid described herein, for example, an alkali or alkaline earth metal salt, for example, a lithium, sodium, potassium, calcium or barium salt or an amine salt, for example, a triethylammonium salt. This reaction is preferably carried out in a substituted sulphoxide or amide solvent for example, in dimethyl sulphoxide, dimethylformamide or hexamethylphosphoramide or, alternatively, an ester may be prepared by reaction of the acid with the alcohol in the presence of a condensing agent, for example, dicyclohexylcarbodiimide.

A stannyl ester may be formed by reaction of a carboxylic acid of formula I or another free acid described herein, or a salt thereof with a reactive tetravalent tin compound, especially a trialkyl tin oxide.

The present invention also provides the salts of those compounds of formula I that have salt-forming groups, especially the salts of free acids of formula I and the acid addition salts of compounds of formula I having a basic group. The salts are especially physiologically tolerable salts, for example, alkali metal and alkaline earth metal salts, for example, sodium, potassium, lithium, calcium and magnesium salts, ammonium salts and salts with an organic amine; also physiologically tolerable acid addition salts. These may be formed with suitable inorganic and organic acids, for example, hydrochloric acid, sulphuric acid, organic carboxylic and organic sulphonic acids, for example, trifluoroacetic acid and p-toluene-sulphonic acid. Some compounds of formula I which contain a basic centre may exist as Zwitterions; such salts are also part of this invention. A salt of a free acid of formula I may be produced by reacting the free acid with the appropriate base in a solvent, preferably under conditions under which the salt precipitates. A preferred base is potassium ethyl hexanoate.

A salt may be produced directly from an ester by splitting off the ester group under suitable reaction conditions, for example, catalytic reduction of an ester, for example, a p-nitrobenzyl ester, in an aqueous/organic solvent, for example, comprising water and ethyl acetate, dioxane, or tetrahydrofuran, in the presence of a metal salt, especially a bicarbonate, for example, in an equivalent amount or in a slight excess, yields a salt directly.

Compounds of the general formula I may be produced, for example, as shown in the reaction scheme overleaf.

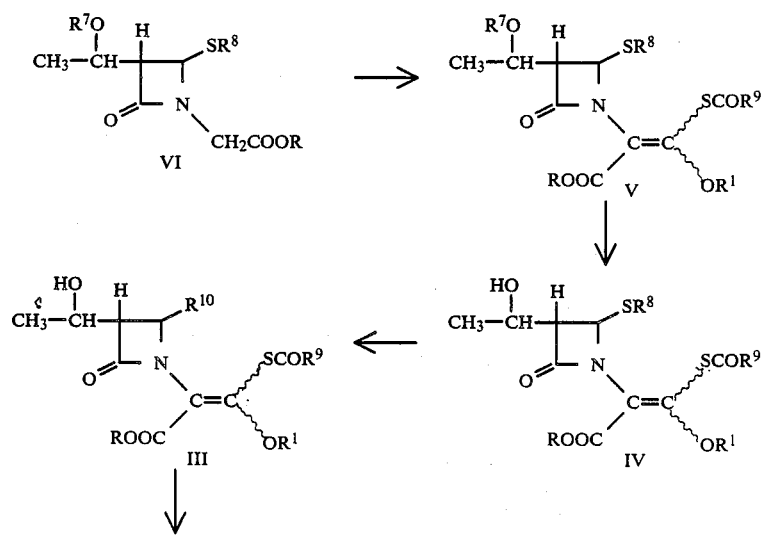

[Structures: Compound II (HO-CH(CH3)- substituent on β-lactam with S, N, OR, COOR) → Compound I (R²C(=O)-O-CH(CH3)- substituent on β-lactam with S, N, OR¹, COOR)]

in which

R, $R^1$ and $R^2$ are defined as above;

$R^7$ represents a hydroxy protecting group;

$R^8$ represents an alkyl group having from 1 to 8, preferably from 1 to 4 carbon atoms, an alkenyl group having up to 4 carbon atoms, or a phenyl group;

$R^9$ represents an alkyl group having from 1 to 4 carbon atoms or a phenyl group; and $R^{10}$ represents a chlorine or bromine atom.

A compound of the general formula VI may be prepared as described in UK Patent Specification No. 2 102 798.

A compound of formula VI may be converted into a compound of formula V by reaction, in the presence of a base, with a compound of formula VII $$Cl-\overset{S}{\underset{\|}{C}}-OR^1 \quad \text{VII}$$

in which $R^1$ is as defined above, followed by reaction with an activated carboxylic acid derivative which comprises the group $R^9$ for example, a compound of formula VIII $$R^9-\overset{O}{\underset{\|}{C}}-Cl \quad \text{VIII}$$

in which $R^9$ is as defined above.

Some compounds of formula VII are known and some are new. New compounds may be prepared by processes analogous to those for the preparation of the known compounds. cf. River & Schalch, Helv. Chem. Acta, Vol. 6, 1923, p. 605, and Reich & Martin, Chem Berichte, Vol 98, 1965 p. 2063.

The reaction between compound VII and compound VI is carried out in the presence of a base, preferably having a $pK_a \geq 20$, preferably a metallated amine, and examples of preferred bases are lithium diisopropylamide, lithium hexamethyldisilazide, lithium 6,6,2,2-tetramethylpiperidide, lithium cyclohexyl isopropylamide, and sodamide.

The reaction is generally carried out in an aprotic solvent, for example, an oxygenated hydrocarbon, preferably an ether, for example, diethyl ether, tetrahydrofuran, dioxane, glyme or diglyme. The reaction temperature is, for example, from −120° to +30° C., preferably from −100° to −40° C.

The amount of base used is, for example, from 1 to 3 moles, calculated per mole of compound VI, preferably from 1.5 to 2.5 moles of base.

The compound of formula VII is preferably used in an amount of from 1 to 1.5 moles per mole of compound VI, preferably from 1 to 1.1 moles of compound VII.

The reaction is preferably carried out as follows: to a stirred solution of compound VI under an inert atmosphere is added the base and subsequently a solution of compound VII in the same or a different solvent.

The activated acid derivative, preferably of formula VIII is preferably added to the mixture resulting from the reaction of compounds VI and VII, especially in an amount of from 1 to 2 moles calculated on compound VI. The reaction is preferably carried out at a temperature of from −80° to +40° C., adding the compound formula VIII to the reaction mixture at the temperature at which the reaction between compounds VI and VII took place, and then warming, or allowing the mixture to warm, to room temperature, if desired, heating the mixture to a temperature of up to 40° C.

The $-SCOR^9$ group in the resulting compound of formula V may be cis or trans to the −COOR group. The isomers may be separated for the subsequent reaction, but this is not generally necessary, and the isomeric mixture is generally used.

Preferred hydroxy-protecting groups $R^7$ are those which are compatible with the synthesis of the compound of formula V and which may be removed under reaction conditions in which the resulting compound IV is stable. Compound IV has been found to be stable in the presence of a proton source, for example, hydrogen chloride, aqueous hydrochloric acid or aqueous hydrofluoric acid. Accordingly, one type of preferred hydroxy protecting groups $R^7$ are those which may be removed under acidic conditions. Such groups are well known in the art and are, for example, tetrahydropyranyl and tetrahydrofuranyl groups; acetal and ketal groups, for example, of formula $$\underset{R^{12}}{\overset{}{\diagup}}\overset{-C-OR^{11}}{\underset{R^{13}}{\diagdown}}$$

in which $R^{12}$ and $R^{13}$, which may be the same or different, each represents a hydrogen atom or a lower alkyl group, preferably a methyl group, or $R^{12}$ and $R^{13}$ together with the carbon atom to which they are attached, represent a cycloalkyl ring having from 4 to 7 carbon atoms, or a tetrahydropyranyl or tetrahydrofuranyl ring, and $R^{11}$ represents a lower alkyl group, preferably a methyl or ethyl group; also silyl esters, for example, as described above in relation to R, for example, $-SiR^{14}R^{15}R^{16}$ groups, in which $R^{14}$, $R^{15}$ and $R^{16}$, which may be the same or different, each represents a lower alkyl group or an aryl group, for example, triethylsilyl, t-butyldimethylsilyl and methyldiphenylsilyl groups; and stannyl groups, for example, as described above in relation to R, for example, $-SnR^{17}R^{18}R^{19}$ groups, in which $R^{17}$, $R^{18}$ and $R^{19}$, which may be the same or different, each represents a lower alkyl group, for example, a tri-n-butylstannyl group. Preferred hydroxy protecting groups $R^7$ are tetrahydropyranyl, 2-methoxyprop-2-yl, trimethylsilyl, triethylsilyl and, especially, t-butyldimethylsilyl groups.

Such groups may be removed by acid hydrolysis, for example, using moderately concentrated hydrochloric acid, e.g. 6M HCl, e.g. in tetrahydrofuran (cf. Belgian Patent Specification No. 881 012); t-Bu$_4$NF in an acidic medium e.g. in acetic acid (cf Belgian Patent Specification No. 882 764): or aqueous hydrogen fluoride e.g. in the presence of acetonitrile (cf J. Chem. Soc. Perkin 1, 1981, 2055).

The halogenation of compound IV to give compound III is carried out with an agent capable of splitting a carbonsulphur bond and introducing a halogen atom. Such agents are well known in the art and include, for example, molecular chlorine, molecular bromine, sulphuryl chloride, sulphuryl bromide, t-butylhypochlorite, cyanogen chloride, and cyanogen bromide.

The reaction is generally carried out at a temperature within the range of from $-40°$ to $+20°$ C. The reaction is generally carried out in a solvent or diluent that is non-protic and is inert under the reaction conditions, for example, an ether, a hydrocarbon or a halogenated hydrocarbon, for example, dioxane, benzene, chloroform or methylene chloride. A mixture of two or more solvents may be used. Examples of halogenating systems are: chlorine in chloroform and, especially, chlorine in benzene and t-butylhypochlorite in benzene.

In the latter two cases, the temperature is preferably from 5° to 20°, and especially from 5° to 10° C. Generally 1 to 2 moles of halogenating agent are used per mole of compound IV (cf. S. Kukolja J. Amer. Chem. Soc. (1971) 93 6267, and P. C. Cherry, C. E. Newall and N. S. Watson, J. C S. Chem. Comm. 1979 p. 663).

A compound of formula III may be converted into a compound of formula II by reaction with a base. The base must be capable of splitting the thio-carbonyl bond in a compound of formula III and of bringing about ring closure. The base may be inorganic or organic, for example, ammonia, or an alkali metal, especially a sodium or potassium, carbonate, bicarbonate, or hydroxide; a primary amine, for example, methylamine, ethylamine, aniline or benzylamine; an alkali metal alkoxide in the corresponding alcohol, for example, sodium methoxide in methanol; or a heterocyclic base, for example, having a pK$_a$ within the range of from 5 to 9, for example, imidazole or pyridine or a substituted pyridine, for example, an alkyl, amino, or alkylamino-substituted pyridine, for example, 4-methyl-, or 4-dimethylamino-pyridine. Imidazole is particularly preferred.

The reaction is generally carried out in a solvent or diluent, the choice of which is wide, provided that it is inert under the reaction conditions. Examples of solvents and diluents are oxygenated hydrocarbons, for example, alcohols, for example, having up to 4 carbon atoms, for example, methanol and ethanol; ethers, for example having up to 4 carbon atoms, for example, diethyl ether, also tetrahydrofuran and dioxane; ketones, for example, having up to 4 carbon atoms, for example, acetone and methyl ethyl ketone; esters, for example, methyl acetate and ethyl acetate; and amides, for example, dimethylformamide and dimethylacetamide; also chlorinated hydrocarbons, for example, chloroform, methylene chloride and carbon tetrachloride; aromatic hydrocarbons, for example, benzene and toluene; and other solvents for example, acetonitrile and nitromethane. A mixture of any two or more solvents may be used, and solvents are preferably used in admixture with water, preferably a water-miscible solvent in admixture with 5 to 20% (v/v) water, especially a mixture of dioxan and water, preferably 5 to 10% (v/v) water. The reaction is generally carried out at a temperature within the range of from 0° to 40° C., preferably from 0° to 20° C.

A compound of formula II is then acylated to give a compound of formula I as described above.

When a compound of formula V having S-stereochemistry at the 3-position is used it has been found that the resulting compound of formula I is predominantly the desired 5R,6S isomer. The following reaction scheme illustrates the stereochemistry, R, R$^1$, R$^7$, R$^8$, R$^9$ and R$^{10}$ being defined as above.

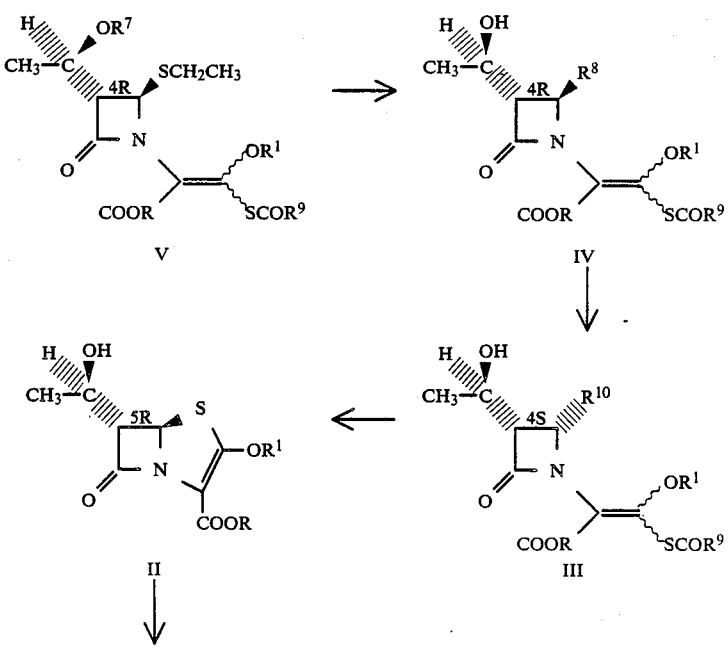

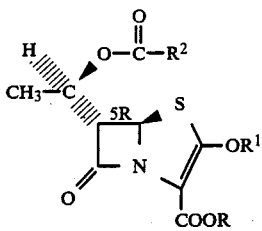

I

Halogenation of the 4R compound of formula IV gives predominantly the 4S compound of formula III. The proportion 4S:4R compound III depends on the halogenating agent used and the reaction conditions, but in general varies from 3:1 to amounts as high as 9:1. The 4R and 4S isomers can be separated readily, for example, by chromatography. Compound III also has E/Z isomerism at the double bond, and the 4R and 4S isomers may be further separated into the individual E and Z isomers. This is not generally necessary, but the 4R and 4S isomers are preferably separated before conversion into a compound of formula II. As can be seen from the reaction scheme, a 4S compound III is converted by reaction with a base into a 5R compound of formula II and subsequently into a 5R compound of formula I.

It is preferable to ensure that any free carboxyl group in any of compounds II to VI is esterified, the ester group preferably being removed after the formation of compound I. Although an ester group may be introduced immediately prior to the formation of compound I, it is preferably to esterify the carboxyl group at an earlier stage in the preferred reaction sequence, for example, to esterify a free carboxyl group in a compound of formula V or VI to ensure that the carboxyl group does not take part in any of the subsequent reactions. An esterifying group may be transesterified to another ester group having more desirable properties for a particular stage of the reaction sequence.

Furthermore, it is advisable to protect any reactive moiety present in R or $R^1$ so that such a moiety does not react with any of the reagents used in any subsequent reaction. Examples of moieties which may require protection are hydroxy, carboxy and amine moieties which may, for example react with the reagents used to convert a compound VI to a compound V. Groups suitable for protecting such reactive moieties are well known, as are methods for their removal. (cf. Protective Groups in Organic Chemistry, editor J. F. W. McOmie, Plenum Press, 1973).

Hydroxy-protecting groups are exemplified above.

Carboxy-protecting groups are, for example, as described above for R. Amino protecting groups are, for example, t-butyloxycarbonyl, benzyloxycarbonyl, p-nitrobenzyloxycarbonyl, p-nitrobenzenesulphenyl and trityl groups.

Reactive moieties may be protected at any appropriate point in the reaction sequence, and the protective groups are preferably removed after the formation of the compound of formula I, for example, if R in formula I represents an esterifying group, this may be removed in the usual manner, depending on the nature of the ester group, for example, by hydrolysis, reduction, or enzymatically, to yield the free acid. A free acid or an ester may be converted into a salt, especially a physiologically tolerable salt, or a salt may be converted into another salt or the free acid or an ester. An ester may be transesterified, or a free acid converted into an ester, for example, to give an ester capable of removal under physiological conditions. Examples of such procedures are given above.

The invention also provides a modification of the process described above, wherein in a compound of formula I, II, III, IV or V or in more than one of these compounds, a substituent of a group $R^1$ is converted at an appropriate point in the reaction sequence into another substituent of $R^1$. A substituent of $R^1$ in compound V, for example, may be converted into another substituent of $R^1$ before the halogenation reaction to give compound III or the initial substituent of $R^1$ may be retained during the halogenation reaction, being converted into another substituent of $R^1$ before the reaction of compound II to give compound I.

The following are examples of interconversions of substituents of $R^1$: ($R^3$ being as defined above).

$R^3S-$ to $R^3SO-$ $R^3S-$ or $R^3SO-$ to $R^3SO_2$ $NO_2-$ to $NH_2-$, which may then be alkylated or acylated, $-CN$ to $-CH_2NH_2$, which may then be alkylated or acylated, $N_3$ to $NH_2-$, which may then be alkylated or acylated, HO— may be alkylated or acylated $R^3CO-O-$ to HO—, which may then be alkylated or acylated.

Halogen to $-SH$, $-SO_2H$, $-SO_3H$, $-CN$ or $CO_2H$, $N_3$ or $-SR$, which may be further treated as described above for the appropriate group. The methods for carrying out such reactions are known in the art, for example, an alkylthio group may be oxidised, preferably with a carboxylic peracid, especially m-chloroperbenzoic acid, to give the corresponding alkylsulphinyl or alkylsulphonyl group; a nitro group may be reduced to an amino group by noble metal catalysed hydrogenation, for example, using platinum, or 10% palladium on carbon, c.f. M. Freifelder, Catalytic Hydrogenation in Organic Synthesis, Willey Interscience, 1978, page 26, and P. N. Rylander, Catalytic Hydrogenation over Platinum Metals, Academic Press, 1967, Chapter 11; an amino group may be alkylated with a conventional alkylating agent, for example, a lower alkyl halide, for example, methyl iodide, or acylated with, for example, an acid chloride or acid anhydride, for example, acetyl chloride or acetic anhydride, a cyano group may be converted into an amino group by reduction, for example, using a metal hydride; an azide group may be converted into an amino group by reduction, for example, using hydrogen sulphide or catalytic reduction; and a hydroxy group may be alkylated or acylated as described above; and a halide, especially an iodide, may be treated with an organometallic compound, for example, an organolithium compound, especially t-butyllithium, the resulting complex being treated with sulphur, sulphur dioxide, cyanogen, or carbon dioxide, to give the —SH, —SO₂H, CN or CO₂H group respectively.

These modifications of the process of the invention are particularly useful for the production of a compound of formula I having a group $R^1$ bearing 1, 2 or 3 substituents, any one or more of which is potentially unstable or incompatible during any one or more of the stages of the reaction sequence described above. The conversion step is, accordingly, carried out after the step in which the substituent is potentially unstable or incompatible.

It will be appreciated that although these modifications are particularly useful for the production of compounds of formula I having substituents on $R^1$ that are potentially unstable in the production process, it is not limited to such groups, and in a further modification of the process of the invention, a substituent of $R^1$ may be produced by conversion of another substituent that does not itself fall within the definition of a substituent of $R^1$, for example, an unsubstituted or substituted, preferably p-nitrosubstituted, benzyloxycarbonylamino group may be converted into a free amino group, for example, by noble metal catalysed hydrogenation, c.f. M. Freifelder, loc. sit., page 111, P. N. Rylander, loc. cit., page 455, and C. Berse et al, J. Org. Chem. 22, 805, 1957.

At each stage of the preferred reaction sequence, the desired compound may be isolated from the reaction mixture and, if desired, purified by appropriate techniques generally used for the purification of organic compounds, for example, chromatography or crystallisation. As indicated above, various intermediates may be produced in the form of mixture of isomers of various kinds. Such a mixture may be separated or resolved at any stage, or the isomeric mixture may be used per se for subsequent reactions. (In the case where a protective group $R^7$ has been removed before halogenation, a resulting compound of formula IV is preferably separated into the 4R and 4S isomers (see below)).

All of the compounds that are provided by the invention may exist in any isomeric form, as discussed above, either as a pure isomer or as a mixture of any two or more isomers.

A compound of formula I may have the R- or S-stereo-chemistry independently at positions 5, 6 and 8. Further isomeric forms will occur when any substituent contains a chiral carbon atom. Any mixture of two or more isomeric forms may be resolved if desired, or a compound of formula I can be used in the form of the isomeric mixture. The preferred stereochemistry at position 5 in compound I is generally R, corresponding to that in naturally occurring penicillins and cephalosporins, at position 6 is S, and at position 8 is R.

The compounds of formula I and salts thereof are β-lactamase inhibitors, and the compounds are generally stable to the action of β-lactamases produced by gram-positive organisms, for example, by *Staphylococcus aureus* and gram negative organisms, for example, *Enterobacter cloacae*. They also possess antibacterial properties themselves and are well absorbed orally. They may be used in humans and other animals, for example, to treat bacterial infections caused by gram-positive and gram-negative bacteria, for example, *Staphylococcus aureus, Streptococcus pyrooenes, Bacillus subtilis, E. coli, Pseudomonas aeruoinosa,* and *Proteus morganii*, some strains of which are penicillin-resistant.

The invention accordingly provides a pharmaceutical preparation which comprises a compound of formula I, or a physiologically tolerable salt thereof, or a mixture of two or more such substances as active ingredient, in admixture or conjunction with a pharmaceutically suitable carrier. The preparation may also comprise one or more other pharmaceutically active substances, for example, another antibacterial substance, especially one which has a β-lactam ring. The preparations may be in a form suitable for enteral or parenteral administration, for example, for oral, intravenous, or intra-muscular administration, for example, as tablets, capsules, syrups, or sterile injectable or infusible solutions. The preparations are advantageously in unit dosage form and preferably comprise from 10 to 2000 mg of the active ingredient. The daily dosage of the active ingredient is generally from 20 to 8000 mg, in divided doses, generally up to 4 doses.

The invention also provides the use of an active ingredient as defined above as a β-lactamase inhibitor and/or as an antibacterial agent.

The invention further provides a pharmaceutical preparation which comprises an active ingredient as defined above, in unit dosage form.

The invention also provides a pharmaceutical preparation which comprises an active ingredient as defined above, or a physiologically tolerable salt thereof or a mixture of two or more such substances, and one or more further pharmaceutically active substances, for example, as described above and, for example, in unit dosage form.

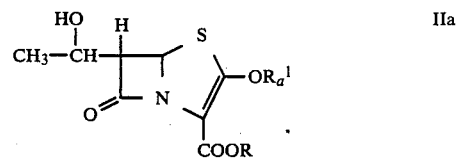

The present invention also provides compounds of the general formula IIa in which R is defined as above, and $R_a^1$ represents a thienyl group which may be unsubstituted or substituted by one, two or three substituents, which may be the same or different, selected from halogen atoms, cyano groups, and lower alkylthio, lower alkylsulphinyl and lower alkylsulphonyl groups. A lower alkylthio group is especially a methylthio group; a lower alkylsulphinyl group is especially a methylsulphinyl group, and a lower alkylsulphonyl group is especially a methylsulphonyl group. Preferably only one substituent is present. The invention also provides those compounds of formula IIa in which R is defined as above $R_a^1$ represents a phenyl group substituted by an ethylthio or ethylsulphinyl group.

Examples of compounds of formula IIa are those in which $R_a^1$ represents a 2-cyano-, 2-methylthio-, 2-methylsulphinyl- or 2-methyl-sulphonylthien-3-yl radical, and those in which $R_a^1$ represents a 4-ethylthio- or 4-ethylsulphinylphenyl group.

The invention further provides salts of compounds of formula IIa.

The invention further provides compounds of the general formulae II, IV and V, in which R, $R^7$, $R^8$, $R^9$ and R[10] are as defined above, and a represents a group $R_a$ as defined above.

Unit dosages are preferably as described above. The following Table provides examples of compounds of the invention.

TABLE

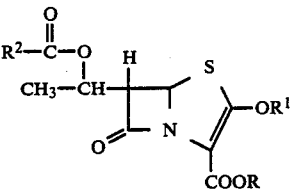

| R | R[1] | R[2] |
|---|---|---|
| H | 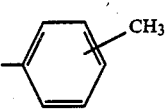 | —CH₃<br>—Ph |
| H | 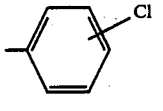 | —CH₃ |
| H | 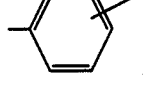 | —CH₃<br>—C₂H₅<br>—C(CH₃)₃<br>—Ph |
| H | 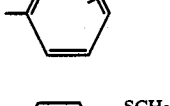 | —CH₃<br>—C₂H₅<br>—C(CH₃)₃<br>—Ph |
| H | 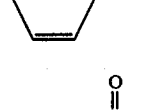 | —CH₃ |
| H | 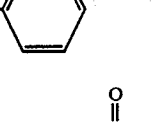 | —CH₃<br>—C₂H₅<br>—C(CH₃)₃<br>—Ph<br>—CH₂OPh |
| H | 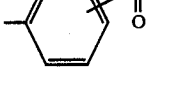 | —CH₃<br>—C₂H₅<br>—C(CH₃)₃<br>—Ph<br>—CH₂OPh |
| H | 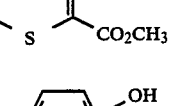 | —CH₃ |
| H | 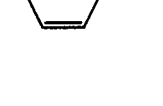 | —CH₃<br>—C₂H₅<br>—C(CH₃)₃<br>—CH₂OPh<br>—Ph |
| | 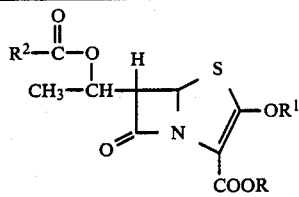 | |

TABLE-continued

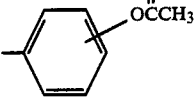

| R | R[1] | R[2] |
|---|---|---|
| H | 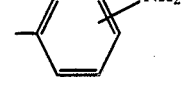 | —Ph<br>—CH₃<br>—C(CH₃)₃<br>—CH₂OPh |
| H | 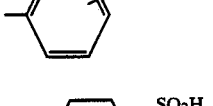 | —Ph<br>—CH₃<br>—C(CH₃)₃<br>—CH₂OPh |
| H | 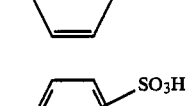 | —CH₃ |
| H | 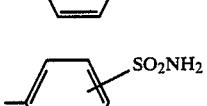 | —CH₃<br>—C(CH₃)₃<br>—Ph |
| H | 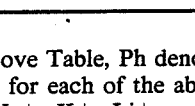 | —CH₃<br>—C(CH₃)₃<br>—Ph |
| H | 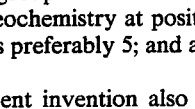 | —CH₃<br>—C₂H₅<br>—C(CH₃)₃<br>—Ph<br>—CH₂OPh |

In the above Table, Ph denotes a phenyl group. Alternatively, for each of the above compounds, R may represent Na⁺, K⁺, Li⁺ or a pivaloyloxymethyl of phthalidyl group.

The stereochemistry at position 5 is preferably R; at position 6 is preferably 5; and at position 8 is preferably R.

The present invention also provides compounds of the general formulae II, II, IV, VI and VII, and more especially provides the compounds specifically described in the Table and in the Examples given hereinafter.

The following Examples illustrate the invention. In them, temperatures are expressed in degrees celsius, and T.L.C. denotes thin layer chromatography.

EXAMPLE 1

2-Methylthio-3-methoxythiophene

To a stirred solution of 21 g of 3-methoxythiophene in diethyl ether at −40° C. was added 115 ml of a 1.6 molar hexane solution of n-butyllithium. The mixture was warmed slowly over 10 minutes to 0° C., then refluxed for 1 hour, was cooled to −78° C. and a solution containing 21.4 g of dimethyldisulphide in 100 ml of diethyl ether was added. The reaction mixture was warmed to room temperature and stirred for 30 minutes, was poured into water and the organic layer washed with water, with brine, and was then dried over magnesium sulphate and evaporated to dryness.

Chromatography over silica gel, eluting with hexane/ethylacetate mixture, afforded 26 g of the title compound as an oil. Yield 91%.

δ(CDCl$_3$): 2.36 (3H, s), 3.92 (3H, s), 6.83 (1H, d, J=5.7 Hz), 7.22 (1H, d, J=5.7 Hz)

EXAMPLE 2

3-Hydroxy-2-methylthiophene

To a stirred solution of 13.8 ml of ethanethiol in dry N,N-dimethylformamide at −78° C. was added 117 ml of a 1.55 molar hexane solution of n-butyllithium. To this mixture was added 10 g of 2-methylthio-3-methoxy-thiophene. The mixture was warmed to room temperature, refluxed for 2 hours, then poured into 2 molar hydrochloric acid and partitioned between ethyl acetate and water. The organic layer was washed with water, with brine and dried over magnesium sulphate, evaporated to dryness.

Chromatography over silica gel, eluting with hexane/ethylacetate mixtures, afforded 6.1 g of the title compound as an oil.

M+ 160.0029

δ(CDCl$_3$): 2.28 (3H, s), 6.00 (1H, bs), 6.74 (1H, d, J=5.7 Hz), 7.22 (1H, d, J=5.7 Hz)

EXAMPLE 3

2-Methylthio-3-thienyl chlorothionoformate

To a vigorously stirred solution of 2.5 g of 3-hydroxy-2-methylthio thiophene and 1.94 ml of thiophosgene in alumina-dried chloroform at 0° C. was added dropwise a solution of 0.88 g of sodium hydroxide in 50 ml of water. The mixture was then warmed to room temperature, was stirred for a further 2 hours, and then partitioned. The organic layer was separated, was washed with ice-cold water, with brine and thoroughly dried over CaCl$_2$. Evaporation in vacuo afforded 2.4 g of an oil.

M+ 225.9102 and 223.9241

δ(CDCl$_3$): 2.42 (3H, s), 6.86 (1H, d, J=5.9 Hz), 7.33 (1H, d, J=5.7 Hz)

EXAMPLE 4

4-Nitrobenzyl 2-(3S-(1R-dimethyl-(2-methyl-2-propyl)silyloxy)ethyl)-4R-ethylthio)azetidin-2-on-1-yl)-3-(2-methylthio-3-thienyloxy)-3-trimethylacetylthio-propenate To a stirred solution of 1.0 g of 4-nitrobenzyl 2-[3(S)-(1(R)-dimethyl-(2-methylprop-2-yl)silyloxyethyl)-4(R)-ethylthioazetidin-2-on-1-yl]-acetate and 0.72 g of 2-methylthio-3-thienyl chlorothionoformate in dry tetrahydrofuran at −100° C. under argon was added a solution of a mixture of 0.89 ml of hexamethyldisilazane and 2.95 ml of a 1.55 molar hexane solution of n-butyllithium in dry tetrahydrofuran. The mixture was stirred at −100° C. for 5 minutes, and 0.84 ml of trimethylacetyl bromide was added. The mixture was allowed to warm to room temperature and was stirred for 2 hours. Acetic acid was then added and the mixture was partitioned between ethyl acetate and water. The organic layer was washed with citric acid, with water, with sodium bicarbonate, with brine, and was then dried over magnesium sulphate and evaporated to dryness.

Chromatography over silica gel, eluting with hexane/ethyl acetate mixtures, afforded 1.1 g of the title compound as a yellow oil.

ν$_{max}$ (CHCl$_3$)=1763 cm$^{-1}$

δ(CDCl$_3$) (for the E/Z mixture): 0.06 (6H, s), 0.81, 0.88 (9H, 2s), 1.0, 1.1 (9H, 2s), 1.25 (3H, t, J=7 Hz), 1.27 (3H, d, J=6 Hz), 2.34, 2.40 (3H, 2s), 2.5–2.8 (2H, m), 3.0–3.3 (1H, m), 4.0–4.4 (1H, m), 5.3 (3H, bs), 6.7 (1H, d, J=5.6 Hz), 7.1 (1H, d, J=5.6 Hz), 7.3–8.2 (4H, m)

EXAMPLE 5

4-Nitrobenzyl 2-(4R-ethylthio-3S-(1R-hydroxyethyl)azetidin-2-on-1-yl)-3-(2-methylthio-3-thienyloxy)-3-trimethylacetylthio-propenate To a stirred solution of 4-nitrobenzyl 2-(3S-(1R-dimethyl(2-methyl-2-propyl)silyloxy)ethyl)-4R-ethylthio)azetidin-2-on-1-yl)-3-(2-methylthio-3-thienyloxy)-3-trimethylacetylpropenate in tetrahydrofuran at room temperature was added 2 ml of water and 2 ml of concentrated hydrochloric acid. The mixture was stirred for 28 hours (when TLC analysis showed the reaction to be complete), and was then partitioned between ethyl acetate and water. The organic layer was washed with sodium bicarbonate, and brine, was dried over MgSO$_4$ and evaporated to dryness.

Chromatography over silica gel and elution with ethyl acetate-hexane mixtures afforded 574 mg of the title compound as a yellow foam.

ν$_{max}$ (CDCl$_3$): 1764 cm$^{-1}$

δ(CDCl$_3$) (for the E/Z mixture): 1.05, 1.09 (9H, 2s), 1.3–1.48 (6H, m), 1.70 (1H, bs), 2.35, 2.40 (3H, 2s), 2.6–2.9 (1H, m), 3.24, 3.30 (1H, 2dd), 4.26–4.37 (1H, m), 5.20–5.44 (3H, m), 6.75–6.77 (1H, 2d, J=5.6 Hz), 7.16 (1H, d, J=5.6 Hz), 7.46–8.25 (4H, m)

EXAMPLE 6

4-Nitrobenzyl 2-(4S-chloro-3S-(1R-hydroxyethyl)azetidin-2-on-1-yl)-3-(2-methylthio-3-thienyloxy)-3-trimethylacetylthio-propenate To a stirred solution of 520 mg of 4-nitrobenzyl 2-[4R-ethylthio-3S-(1R-hydroxyethyl)-azetidin-2-on-1-yl]-3-(2-methylthio-3-thienyloxy)-3-trimethylacetylthio-propenate in dichloromethane at −40° C. was added a solution of 0.73 mmol of chlorine in 1.22 ml of carbon tetrachloride. After 30 minutes the reaction was warmed to room temperature and evaporated to dryness. Chromatography over silica gel and elution with ethyl acetate-hexane mixtures afforded 340 mg of the title compound as a yellow foam.

ν$_{max}$ (CDCl$_3$): 1781 cm$^{-1}$

δ(CDCl$_3$) (for the E/Z mixture): 1.06, 1.09 (9H, 2s), 1.42, 1.46 (3H, 2d, J=6.3 Hz), 1.58 (1H, bs), 4.58 (1H, 2d, J=4.2 Hz and 9 Hz), 4.33–4.50 (1H, m), 5.29, 5.30 (2H, 2s), 6.11, 6.26 (1H, 2d, J=4.2 Hz), 6.75 (1H, d, J=5.8 Hz), 7.20 (1H, d, J=5.8 Hz), 7.46–8.32 (4H, m)

EXAMPLE 7

4-Nitrobenzyl 5R-6S-(1R-hydroxyethyl)-3-(2-methylthio-3-thienyloxy)-7-oxo-4-thia-1-azabicyclo[3,2,0]hept-2-ene-2-carboxylate To a stirred solution of 340 mg of 4-nitrobenzyl 2-[4S-chloro-3S-(1R-hydroxyethyl)azetidin-2-on-1-yl]-3-(2-methylthio-3-thienyloxy)-3-trimethylacetylthio-propenate in dioxan:water (9:1 v/v) at +5° was added 45 mg of imidazole. After 30 minutes at +5° C. the reaction mixture was warmed to room temperature and partitioned between ethylacetate and water. The organic layer was washed with citric acid, with water, with saturated sodium bicarbonate, and with brine, was dried over MgSO$_4$ and then evaporated in vacuo to dryness. Chromatography over silica gel, and elution with hexane-ethyl acetate mixtures afforded 116 mg of the title compound as a yellow foam.

$\nu_{max}$ (CDCl$_3$): 1787, 1791 (sh), 1522 cm$^{-1}$

δ(CDCl$_3$): 1.36 (3H, d, J=6.3 Hz), 1.60 (1H, bs), 2.41 (3H, s), 3.74 (1H, dd, J=1.4 Hz and 6 Hz), 4.21–4.34 (1H, m), 5.30, 5.5 (2H, AB, J=14 Hz), 5.63 (1H, d, J=1.4 Hz), 6.88 (1H, d, J=5.7 Hz), 7.26 (1H, d, J=5.7 Hz), 7.61 (2H, d, J$_{AB}$=8.8 Hz), 8.21 (2H, d, J$_{AB}$=8.8 Hz)

EXAMPLE 8

4-Nitrobenzyl 5R-6S-(1R-hydroxyethyl)-3-(2-methylsulphinyl-3-thienyloxy)-7-oxo-4-thia-1-azabicyclo[3,2,0]hept-2-ene-2-carboxylate To a stirred solution of 116 mg of 4-nitrobenzyl 5R-6S-(1R-hydroxyethyl)-3-(2-methylthio-3-thienyloxy)-7-oxo-4-thia-1-azabicyclo[3,2,0]hept-2-ene-2-carboxylate in ethyl acetate at −78° C. was added a solution of 0.23 mmol of m-chloroperbenzoic acid in ethyl acetate. After 30 minutes the reaction mixture was warmed over a further hour to room temperature, and then washed with sodium bicarbonate solution, with brine, was dried ober MgSO$_4$ and evaporated to dryness. Chromatography over silica gel and eluting with ethyl acetate-hexane mixtures afforded 72 mg of the title compound.

$\nu_{max}$ (CDCl$_3$): 1790, 1797 (sh), 1535 cm$^{-1}$

δ(CDCl$_3$) (mixture of α- and β-sulphoxides): 1.37 (3H, d, J=6.3 Hz), 1.56 (1H, bs), 2.96 (3H, s), 3.80 (1H, dd, J=1.5 Hz and 6 Hz), 4.21–4.37 (1H, m), 5.30, 5.5 (2H, AB, J=14 Hz), 5.69 (1H, 2d, J=1.5 Hz), 6.95 (1H, 2d), 7.57–7.60 (3H, m), 8.21 (2H, d, J$_{AB}$=8.6 Hz)

EXAMPLE 9

4-Nitrobenzyl 5(R),6(S)-(1(R)-acetoxyethyl)-3-(4-methylsulphinyl-phenoxy)-7-oxo-4-thia-1-azabicyclo[3,2,0]hept-2-ene-2-carboxylate To a stirred solution of 151 mg of 4-nitrobenzyl 5(R),6(S)-(1(R)-hydroxyethyl)-3-(4-methylsulphinyl-phenoxy)-7-oxo-4-thia-1-azabicyclo[3,2,0]hept-2-ene-2-carboxylate in 2 ml of dry tetrahydrofuran at 0° C. was added a solution of 3.7 mg of 4-(N,N-dimethylamino)-pyiridine N, and 563 mg of acetic anhydride in 2 ml of dry tetrahydrofuran. After 30 minutes, the reaction mixture was warmed to room temperature, partitioned between ethyl acetate and water; the organic layer was washed with saturated aqueous sodium bicarbonate solution, and with brine, was dried over magnesium sulphate and evaporated in vacuo to dryness. Chromatography of the residue over silica gel, and elution with hexane-ethyl acetate mixtures afforded 99 mg of the title compound.

$\nu_{max}$ (CDCl$_3$): 1795, 1740 (sh) and 1720 cm$^{-1}$

δ(CDCl$_3$): 1.38 (3H, d, J=6 Hz), 2.02 (3H, s), 2.74 (3H, s), 3.90 (1H, dd, J=1.5 Hz and 6 Hz), 5.1–5.4 (3H, m), 5.63 (1H, d, J=1.5 Hz), 7.0–8.3 (8H, m)

EXAMPLE 10

4-Nitrobenzyl 5(R),6(S)-[1(R)-phenoxyacetoxy)ethyl](phenoxyacetoxy)ethyl]-3-(4-methylsulphinylphenoxy)-7-oxo-4-thia-1-aza-bicyclo[3,2,0]hept-2-ene-2-carboxylate 57 mg of the above compound were obtained from 175 mg of 4-nitrobenzyl 5(R),6(S)-(1(R)-hydroxyethyl)-3-(4-methylsulphinylphenoxy)-7-oxo-4-thia-1-azabicyclo[3,2,0]hept-2-ene-2-carboxylate by a procedure analogous to that described in Example 9 using 200 mg of phenoxyacetic anhydride, 40 mg of pyridine, 2 mg of dimethylaminopyridine and 1 ml of dry tetrahydrofuran.

δ(CDCl$_3$): 1.35 (3H, d, J=6 Hz), 2.73 (3H, s), 3.96 (1H, dd, J=1.5 and 6 Hz), 4.4 (2H, m), 5.3 (3H, m), 5.78 (1H, d, J=1.5 Hz), 7.0–8.3 (13H, m)

EXAMPLE 11

Potassium 5(R),6(S)-(1(R)-acetoxyethyl)-3-(4-methylsulphinyl-phenoxy)-7-oxo-4-thia-1-azabicyclo[3,2,0]hept-2-ene-2-carboxylate A mixture of a solution of 55 mg of 4-nitrobenzyl 5(R),6(S)-(1(R)-hydroethyl)-3-(4-methylsulphinyl-phenoxy)-7-oxo-4-thia-1-azabicyclo[3,2,0-hept-2-en-2-carboxylate in dioxan, and 10 mg potassium bicarbonate in water, and 50 mg 10% palladium/charcoal was hydrogenated at 50 p.s.i. until TLC analysis indicated complete reaction. The mixture was filtered through Celite (Trade Mark) and lyophilized to yield 41 mg of the title compound as a crystalline solid.

EXAMPLE 12

Potassium 5(R),6(S)-(1(R)-(phenoxyacetoxy)ethyl)-3-(4-methyl-sulphinylphenoxy)-7-oxo-4-thia-1-azabicyclo[3,2,0-]hept-2-ene-2-carboxylate 34 mg of the above salt were obtained from 40 mg of the corresponding 4-nitrobenzyl carboxylate (see Example 10) by a procedure analogous to that described in Example 11 using 6.3 mg of potassium bicarbonate.

EXAMPLE 13

4-Nitrobenzyl 5(R),6(S)-(1R-(4-chlorobenzoyl)oxyethyl)-3-(4-methyl-sulphinylphenoxy)-7-oxo-4-thia-1-azabicyclo[3,2,0-]hept-2-ene-2-carboxylate 112 mg of the above compound were obtained as an oil from 150 mg of 4-nitrobenzyl 5(R),6(S)-1(R)-hydroxyethyl)-3-(4-methylsulphinylphenoxy)-7-oxo-4-thia-1-azabicyclo[3,2,0]hept-2-ene-2-carboxylate by a procedure analogous to that described in Example 9 using 445 mg of 4-chlorobenzoic anhydride, 5 ml of dichloromethane, and 18.3 mg of 4-dimethylaminopyridine.

δ(CDCl$_3$): 1.56 (3H, d, J=6.5 Hz), 2.74 (3H, s), 4.07 (1H, dd, J=1.4 and 7 Hz), 5.25, 5.40 (2H, AB, J=14 Hz), 5.50–5.56 (1H, m), 5.79 (1H, d, J=1.4 Hz), 7.31–7.37 (4H, m), 7.53 (2H, d, J=9 Hz), 7.68 (2H, d, J=9 Hz), 7.93 (2H, d, J=8.6 Hz), 8.15 (2H, d, J=8.8 Hz)

EXAMPLE 14

Potassium 5(R),6(S)-(1(R)-(4-chlorobenzoyl)oxyethyl)-3-(4-methylsulphinylphenoxy)-7-oxo-4-thia-1-azabicyclo[3,2,0]hept-2-ene-2-carboxylate 66 mg of the above salt were obtained from 112 mg of the corresponding 4-nitrobenzyl carboxylate (as defined in Example 13) by a procedure analogous to that described in Example 11, using 17 mg of potassium bicarbonate and 100 mg of 10% palladium on charcoal.

δ($D_2O$): 1.47 (3H, d, J=6 Hz), 2.86 (3H, s), 4.27 (1H, dd, J=1.5 and 7 Hz), 5.42–5.57 (1H, m), 5.85 (1H, d, J=1.5 Hz), 7.38 (2H, d, J=9 Hz), 7.47 (2H, d, J=9 Hz), 7.72 (2H, d, J=9 Hz), 7.95 (2H, d, J=9 Hz)

EXAMPLE 15

4-Nitrobenzyl 5(R),6(S)-(1(R)-(1-butoxycarbonylaminoacetoxy)ethyl)-3(4-methylsulphinylphenoxy)-7-oxo-4-thia-1-azabicyclo[3,2,0]hept-2-ene-2-carboxylate To a solution of 99 mg of 4-nitrobenzyl 5R,6S-(1R-hydroxyethyl)-3-(4-methylsulphinylphenoxy)-7-oxo-4-thia-1-azabicyclo[3,2,0]hept-2-ene-2-carboxylate and 5 mg of N,N-dimethylaminopyridine in 5 ml dry tetrahydrofuran at 0° C. was added with stirring a freshly prepared solution of 980 ml of N-(t-butoxycarbonyl)glycine anhydride in 5 ml dichloromethane. After two hours at 0° C., the mixture was warmed and stirred a further two hours at room temperature, and then evaporated to dryness. The residue was partitioned between ethyl acetate and water, and the organic layer was washed with saturated sodium bicarbonate solution and brine. Evaporation to dryness and chromatography of the residue over silica gel, and elution with hexane-ethyl acetate mixtures afforded 98 mg of the title compound.

δ($CDCl_3$): 1.46 (3H, d, J=6.5 Hz), 2.73 (3H, s), 3.85 (2H, d, J=5.7 Hz), 4.95 (1H, m), 5.33 (2H, AB, J=14 Hz), 5.35 (1H, m), 5.66 (1H, d, J=1.2 Hz), 7.31 (2H, d, J=9 Hz), 7.55 (2H, d, J=9 Hz), 7.67 (2H, d, J=9 Hz), 8.20 (2H, d, J=9 Hz)

EXAMPLE 16

5R,6S-(1R-(Aminoacetoxy)ethyl)-3-(4-methylsulphinylphenoxy)-7-oxo-4-thia-1-azabicyclo[3,2,0]hept-2-ene-2-carboxylic acid To a stirred solution of 98 mg of 4-nitrobenzyl 5R,6S-(1R-(t-butoxycarbonylaminoacetoxy)ethyl)-3-(4-methylsulpninylphenoxy)-7-oxo-4-thia-1-azabicyclo[3,2,0]hept-2-ene-2-carboxylate in a mixture of chloroform and 2,2,2-trifluoroethanol at −20° C. was added 5 μl of trifluoroacetic acid. The mixture was then warmed to room temperature, and then partitioned at 0° C. between chloroform and aqueous potassium bicarbonate solution. The organic layer was separated and rapidly washed with water, was dried over magnesium sulphate, and rapidly evaporated in vacuo. The residue was dissolved in 10 ml of dioxane; 10 ml of ice-water, and 50 mg of 10% palladium on charcoal were added, and the mixture was hydrogenated. The mixture was then filtered through "Hiflo" (Trade Mark, diatomaceous earth); the filter cake was washed well with water. The filtrate was lyophilised to afford 43 mg of the title compound.

EXAMPLE 17

4-Nitrobenzyl 5(R),6(S)-(1-(R)-acetoxyethyl)-3-(4-fluorophenoxy)-7-oxo-4-thia-1-azabicyclo[3,2,0]hept-2-ene-2-carboxylate To a stirred solution of 100 mg of 4-nitrobenzyl 5(R)-3-(4-fluorophenoxy)-6(S)-(1(R)-hydroxyethyl)-7-oxo-4-thia-1-azabicyclo[3,2,0]hept-2-ene-2-carboxylate in 3 ml of tetrahydrofuran at 0° C. was added a solution of 3 mg of dimethylaminopyridine in 0.5 ml of acetic anhydride. After 30 minutes, the reaction mixture was warmed to room temperature, partitioned between ethyl acetate and water, the organic layer was washed with saturated sodium bicarbonate solution and brine, dried over magnesium sulphate, and evaporated in vacuo to dryness. Chromatography over silica gel and elution with ethyl acetate-hexane mixtures afforded 74 mg of the title compound.

δ($CDCl_3$): 1.40 (3H, d, J=6 Hz), 2.01 (3H, s), 3.80 (1H, dd, J=1.5 Hz, 6 Hz), 4.99–5.26 (1H, m), 5.19 (2H, q), 5.51 (1H, d, J=1.5 Hz), 6.87–7.23 (4H, m), 7.34–8.22 (4H, m),

EXAMPLE 18

Potassium 5(R),6(S)-(1-(R)-acetoxyethyl)-3-(4-fluorophenoxy)-7-oxo-4-thia-1-azabicyclo[3,2,0]hept-2-ene-2-carboxylate 47 g of the above salt were obtained from 74 mg of the corresponding 4-nitrobenzyl carboxylate (see Example 17) by a procedure analogous to that described in Example 11, using 14 mg of potassium bicarbonate and 100 mg of 10% Pd on carbon.

EXAMPLE 19

4-Nitrobenzyl 2-[3(S)-(1R)-dimethyl-(2-methylprop-2-yl)silyloxyethyl)-4(R)-ethylthio-azetidin-2-on-1-yl]-3-(4-ethylthiophenoxy)-3-trimethylacetylthiopropenate 1.29 g of the above compound were obtained as an orange oil from 1.0 g of 4-nitrobenzyl 2-[3S-(1R-dimethyl-(2-methyl-2-propyl)-siloxyethyl)-4R-ethylthio-azetidin-2-on-yl]acetate by a procedure analogous to that described in Example 4 using 1.47 g of 4-ethylthiophenyl chlorothionoformate, 1.12 ml of hexamethyldisilazane, 5.31 mmol of n-butyllithium, and 0.77 ml of trimethylacetyl bromide.

$\nu_{max}$ ($CDCl_3$): 1770 cm$^{-1}$

δ($CDCl_3$): 0.01 (6H, s), 0.82, 0.88 (9H, 2s), 1.06, 1.10 (9H, 2s), 1.27–1.49 (9H, m), 2.37–3.07 (4H, m), 3.15 (1H, dd, J=2 Hz and 4 Hz), 4.06–4.57 (1H, m), 5.25 (3H, bs), 6.89–7.22 (4H, m), 7.40, 8.03 (4H, AB, J=8 Hz)

EXAMPLE 20

4-Nitrobenzyl 2-[4(R)-ethylthio-3(S)-(1(R)-hydroxyethyl)azetidin-2-on-1-yl]-3-(4-ethylthiophenoxy)-3-trimethylacetylthiopropenate 3.14 g of the above compound were obtained from 6.2 g of the corresponding 1(R)-dimethyl-(2-methylprop-2-yl)silyloxyethyl compound (defined in Example 19) by a procedure analogous to that described in Example 5, using 6.3 ml of water and 69 mmols of concentrated hydrochloric acid.

$\nu_{max}$ ($CDCl_3$): 1767 cm$^{-1}$

δ($CDCl_3$): 1.05, 1.09 (9H, 2s), 1.10–1.38 (9H, m), 2.54–3.06 (4H, m), 3.23 (1H, dd, J=2.0 and 4.0 Hz), 4.05–4.32 (1H, m), 5.33 (3H, bs), 6.87–7.40 (4H, m), 7.48–8.26 (4H, m)

EXAMPLE 21

4-Nitrobenzyl 2-[4(S)-chloro-3(S)-(1(R)-hydroxyethyl)azetidin-2-on-1-yl]-3-(4-ethylthiophenoxy)-3-trimethylacetylthiopropenate 2.26 g of the above compound were obtained as a pale yellow foam from 3.14 g of the corresponding 4(R)-ethylthio compound (defined in Example 20) by a procedure analogous to that described in Example 6, using 5.8 mmol of chlorine in carbon tetrachloride.

$\nu_{max}$ (CDCl$_3$): 1730, 1780 cm$^{-1}$ $\delta$(CDCl$_3$): 1.03, 1.07 (9H, 2s), 1.27 (3H, t, J=7 Hz), 1.38 (3H, d, J=6 Hz), 2.40 (1H, bs), 2.91 (2H, q, J=7 Hz), 3.50 (1H, dd, J=4 and 9 Hz), 4.03–4.47 (1H, m), 5.28 (2H, s), 6.13 (1H, d, J=4 Hz), 6.80–7.31 (4H, m), 7.38–8.23 (4H, m)

EXAMPLE 22

4-Nitrobenzyl 5(R)-3-(4-ethylthiophenoxy)-6(S)-(1(R)-hydroxyethyl)-7-oxo-4-thia-1-azabicyclo[3,2,0]hept-2-ene-2-carboxylate 0.92 g of the above compound were obtained as a white crystalline solid from 2.26 g of the corresponding 4(S)-chloro-3(S)-(1(R)-hydroxyethyl)-azetidinone derivative (defined in Example 21) by a procedure analogous to that described in Example 7 using 7.25 mmol of imidazole.

$\nu_{max}$ (CDCl$_3$): 1788 cm$^{-1}$ $\delta$(CDCl$_3$): 1.29–1.36 (6H, m), 2.94 (2H, q, J=7.35 Hz), 3.74 (1H, dd, J=1.1 and 6.4 Hz), 4.21–4.26 (1H, m), 5.24, 5.42 (2H, AB, J=14 Hz), 5.61 (1H, d, J=1.1 Hz), 7.09 (2H, d, J=8 Hz), 7.31 (2H, d, J=8 Hz), 7.56 (2H, d, J=8 Hz), 8.18 (2H, d, J=8 Hz)

EXAMPLE 23

4-Nitrobenzyl 5(R),6(S)-(1(R)-benzoyloxyethyl)-3-(4-cyanophenoxy)-7-oxo-4-thia-1-azabicyclo[3,2,0]hept-2-ene-2-carboxylate 70 mg of the above compound were obtained from 100 mg of 4-nitrobenzyl 5(R)-3-(4-cyanophenoxy)-6(S)-(1(R)-hydroxyethyl)-7-oxo-4-thia-1-azabicyclo[3,2,0]hept-2-ene-2-carboxylate by a procedure analogous to that described in Example 17, using 1 ml of dry tetrahydrofuran, 1 ml of dimethylaminopyridine, 33 mg of benzoyl anhydride and 18 g of pyridine.

$\delta$(CDCl$_3$): 1.3 (3H, d, J=6 Hz), 3.95 (1H, dd, J=1.5 and 6 Hz), 5.29 (3H, m), 5.8 (1H, d, J=1.5 Hz), 7.0–8.2 (13H, m)

EXAMPLE 24

Potassium 5(R),6(S)-{1(R)-benzoyloxyethyl}-3-(4-cyanophenoxy)-7-oxo-4-thia-1-azabicyclo[3,2,0]hept-2-ene-2-carboxylate 48 mg of the above salt were obtained from 65 mg of the corresponding 4-nitrobenzyl carboxylate (see Example 23) by a procedure analogous to that described in Example 11, using 11.4 mg of potassium bicarbonate.

EXAMPLE 25

4-Nitrobenzyl 5(R),6(S)-{1(R)-acetoxyethyl}-3-(4-cyanophenoxy)-7-oxo-4-thia-1-azabicyclo[3,2,0]hept-2-ene-2-carboxylate Using a procedure analogous to that described in Example 17, 122 mg of the title compound were obtained from 150 mg of 4-nitrobenzyl 5(R),3-(4-cyanophenoxy)-6(S)-{1(R)-hydroxyethyl}-7-oxo-4-thia-1-azabicyclo[3,2,0]hept-2-ene-2-carboxylate using 600 μl of acetic anhydride, 20 mg of dimethylaminopyridine and 5 ml of dry tetrahydrofuran.

$\nu_{max}$ (CDCl$_3$): 2240, 1795 and 1720 cm.

$\delta$(CDCl$_3$): 1.43 (3H, d J=6.4 Hz), 2.05 (3H, s), 3.96 (1H, dd J=1.5 and 7.6 Hz), 5.22 and 5.38 (2H, AB J=13.6 Hz), 5.29 (1H, m), 5.70 (1H, d J=1.5 Hz), 7.22 (2H, d J=8.9 Hz), 7.52 (2H, D J=8.8 Hz), 7.69 (2H, d J=8.9 Hz), 8.20 (2H, d J=8.8 Hz)

EXAMPLE 26

Potassium 5(R),6(S)-{1(R)-acetoxyethyl}-3-(4-cyanophenoxy)-7-oxo-4-thia-1-azabicyclo[3,2,0]hept-2-ene-2-carboxylate 71 mg of the above salt were obtained from 106 mg of the corresponding 4-nitrobenzyl ester (see example 25) by a procedure analogous to that described in Example 11, using 21 mg of potassium bicarbonate, 106 mg of 10% palladium on carbon, 5 ml of dioxan, and 5 ml of water.

$\delta$(D$_2$O): 1.42 (3H, d J=6.5 Hz), 2.17 (3H, s), 4.27 (1H, dd J=1.5 and 5.3 Hz), 5.35 (1H, m), 5.87 (1H, d J=1.5 Hz), 7.40 (2H, d J=9 Hz), 7.87 (2H, d J=9 Hz)

EXAMPLE 27

4-Nitrobenzyl 5(R),6(S)-{1(R)-(cyclopropylcarbonyloxy)ethyl}-3-(4-methylsulphinylphenoxy)-7-oxo-1-azabicyclo[3,2,0]hept-2-ene-2-carboxylate A mixture of 100 mg of 4-nitrobenzyl 5(R),6(S)-(1R-hydroxyethyl)-3-(4-methylsulphinylphenoxy)-7-oxo-1-azabicyclo[3,2,0]hept-2-ene-2-carboxylate, 500 mg of cyclopropane carboxylic anhydride, 16 mg of pyridine, 5 mg of 4-N,N-dimethylaminopyridine and 3 ml of tetrahydrofuran was stirred at room temperature for one hour, was then evaporated in vacuo at 0° C., and partitioned between ethyl acetate and water. The organic layer was washed with water, was dried Na$_2$SO$_4$, was evaporated in vacuo and chromatographed on silica gel. Elution with ethyl acetate/hexane mixtures afforded 73 mg of the title compound as a pale oil.

$\nu_{max}$(CDCl$_3$): 1797 cm$^{-1}$ $\delta$(CDCl$_3$): 0.8–1.2 (4H, m), 1.35 (3H, d, J=7 Hz), 1.35–1.8 (1H, m), 2.73 (3H, s), 3.81 (1H, dd J=1.5 Hz and 6 Hz), 3.85 (1H, m), 5.31 (2H, d+d, J$_{gem}$=14 Hz), 5.73 (1H, d J=1.5 Hz), 7.1–8.3 (8H, m)

EXAMPLE 28

4-Nitrobenzyl 5(R),6(S)-(1R-methoxyacetoxyethyl)-3-(4-methylsulphinylphenoxy)-7-oxo-4-thia-1-azabicyclo[3,2,0]hept-2-ene-2-carboxylate By a procedure analogous to that described in Example 27 and using 100 mg of the corresponding hydroethylpenem, 500 mg of methoxyacetic anhydride, 16 mg of pyridine, 5 mg of 4-N,N-dimethylaminopyridine and 3 ml of tetrahydrofuran there were obtained 39 mg of the title compound.

$\nu_{max}$(CDCl$_3$): 1797, 1745 cm$^{-1}$ $\delta$(CDCl$_3$): 1.34 (3H, d, J=Hz), 2.73 (3H, s), 3.47 (3H, s), 3.75 (2H, s), 3.80 (1H, dd, J=1.5 Hz and 6 Hz), 3.9–4.4 (1H, m), 5.31 (2H, d+d, J$_{gem}$=14 Hz), 5.74 (1H, d, J=1.5 Hz), 7.1–8.3 (8H, m)

EXAMPLE 29

4-Nitrobenzyl 5(R),3-(4-methylsulphinylphenoxy)-7-oxo-6(S)-{1(R)-(p-toluoyloxy)ethyl}-4-thia-1-azabicyclo[3,2,0]hept-2-ene-2-carboxylate To a solution of 100 mg of the corresponding hydroxyethylpenem in 1 ml of dichloromethane at 0° was added 5 mg of 4-dimethylaminopyridine, 87 μl of 4-toluoyl chloride and 54 μl of pyridine. The mixture was warmed to room temperature, was stirred for one hour and then evaporated in vacuo. Chromatography of the residue over silica gel, and elution with hexane-ethyl acetate mixtures afforded 34 mg of the title compound as an oily solid.

$\nu_{max}$(CDCl$_3$): 1788, 1727 cm$^{-1}$ $\delta$(CDCl$_3$): 1.34 (3H, d J=6 Hz), 2.43 (3H, s), 2.73 (3H, s), 3.74 (1H, dd J=1.5 Hz and 5.7 Hz), 5.34 (3H, m including J$_{gem}$=13.7 Hz), 5.61 (1H, d J=1.5 Hz), 7.0–8.3 (12H, m)

EXAMPLE 30

Potassium 5(R),3-(4-methylsulphinyloxyphenoxy)-7-oxo-6(S)-{1(R)-(p-toluoyloxy)ethyl}-4-thia-1-azabicyclo[3,2,0]hept-2-ene-2-carboxylate A mixture of 30 mg of the corresponding 4-nitrobenzyl penem, 4.8 mg of KHCO$_3$, 2 ml of dioxane, 2 ml water and 30 mg of 10% palladium on charcoal was hydrogenated at 50 psi with vigorous shaking for 1 hour. The mixture was then filtered through "Hiflo" (Trade Mark, diatomaceous earth) and the filter cake was washed well with water. The filtrate was lyophilised to afford 20 mg of the title compound.

EXAMPLE 31

Potassium 5(R),6(S)-{1(R)-(cyclopropylcarbonyloxy)ethyl}-3-(4-methylsulphinylphenoxy)-7-oxo-1-azabicyclo[3,2,0]hept-2-ene-2-carboxylate By a procedure analogous to that described in Example 30, using 50 mg of the corresponding 4-nitrobenzyl ester, 8.7 mg of KHCO$_3$, 2 ml dioxan, 2 ml water, and 50 mg of 10% palladium on charcoal, there were obtained 35 mg of the title compound.

EXAMPLE 32

Potassium 5(R),6(S)-(1R-methoxyacetoxyethyl)-3-(4-methylsulphinylphenoxy)-7-oxo-4-thia-1-azabicyclo[3,2,0]hept-2-ene-2-carboxylate By a process analogous to that described in Example 30, using 35 mg of the corresponding 4-nitrobenzyl ester, 6.1 mg of KHCO$_3$, 2 ml of dioxan, 2 ml of water, 30 mg of 10% palladium on charcoal, there were obtained 28 mg of the title compound.

EXAMPLE 33

4-Nitrobenzyl 5R-6S-(1R-hydroxyethyl)-3-(2-methylsulphonyl-3-thienyloxy)-7-oxo-4-thia-1-azabicyclo[3,2,0]hept-2-ene-2-carboxylate To a stirred solution of 300 mg of 4-nitrobenzyl 5R-6S-(1R-hydroxyethyl)-3-(2-methylsulphinyl-3-thienyloxy)-7-oxo-4-thia-1-azabicyclo[3,2,0]hept-2-ene-carboxylate in ethylacetate at −40° C. was added a solution of 0.59 mmol of m-chloroperoxybenzoic acid in ethylacetate. After 30 minutes the reaction mixture was warmed to room temperature and washed with saturated sodium bicarbonate, with brine, dried over MgSO$_4$, and then evaporated to dryness. Chromatography over silica gel and elution with hexane ethylacetate mixtures afforded the title compound (54 mg) as a yellow foam.

$\gamma_{max}$(CDCl$_3$): 1790, 1797 (sh); 1525 cm$^{-1}$ $\delta$(CDCl$_3$): 1.37 (3H, d, J=6.3 Hz), 1.57 (1H, bs), 3.28 (3H, s), 3.86 (1H, dd, J=1.4 and 6.5 Hz), 4.21–4.36 (1H, m), 5.24, 5.48 (2H, AB, J=14 Hz), 5.72 (1H, d, J=1.4 Hz), 6.98 (1H, d, J=5.3 Hz), 7.54–7.68 (3H, m), 8.20 (2H, d, J$_{AB}$=8.8 Hz)

EXAMPLE 34

Potassium 5R-6S-(1R-hydroxyethyl)-3-(2-methylsulphonyl-3-thienyloxy)-7-oxo-4-thia-1-azabicyclo[3,2,0]hept-2-ene-2-carboxylate 40 mg of the above salt were obtained from 50 mg of the corresponding 4-nitrobenzyl carboxylate (see Example 33) by a procedure analogous to that described in Example 11 using 9.5 mg of potassium bicarbonate.

$\delta$(D$_2$O): 1.27 (3H, d, J=6.4 Hz), 3.41 (3H, s), 3.97 (1H, dd, J=1.4 Hz and 6 Hz), 4.18–4.32 (1H, m), 5.72 (1H, d, J=1.3 Hz), 7.19 (1H, d, J=5.5 Hz), 7.85 (1H, d, J=5.5 Hz)

EXAMPLE 35

4-Nitrobenzyl 5(R)-3-(4-ethylsulphinylphenoxy)-6(S)-(1(R)-hydroxyethyl)-7-oxo-4-thia-1-aza-bicyclo[3,2,0]hept-2-ene-2-carboxylate 382 mg of the above compound were obtained from 525 mg of the corresponding 4-ethylthiophenoxy compound (defined in Example 22) by a procedure analogous to that described in Example 8, using 0.17 mmol of 3-chloroperoxybenzoic acid.

$\delta$(CDCl$_3$): 1.20 (3H, t J=7.4 Hz), 1.38 (3H, d J=6.3 Hz), 1.58 (1H, bs), 2.76, 2.91 (2H, ABq J=7.4 Hz, J$_{AB}$=14 Hz), 3.80 (1H, dd J=1.3 and 6.7 Hz), 4.26–4.32 (1H, m), 5.23, 5.44 (2H, AB J=14 Hz), 5.69 (1H, d J=1.3 Hz), 7.30 (2H, d J=8.6 Hz), 7.55 (2H, d J=8.6 Hz), 7.63 (2H, d J=8.7 Hz), 8.19 (2H, d J=8.7 Hz)

EXAMPLE 36

Potassium 5R-6S-(1R-hydroxyethyl)-3-(2-methylsulphinyl-3-thienyloxy)-7-oxo-4-thia-1-azabicyclo[3,2,0]hept-2-ene-2-carboxylate 44 mg of the above salt were obtained from 72 mg of the corresponding 4-nitrobenzyl carboxylate (see Example 8) by a procedure analogous to that described in Example 11 using 14.1 mg of potassium bicarbonate.

δ(D₂O): (mixture of α- and β-sulphoxides), 1.28 (3H, d, J=6.3 Hz), 3.09 (3H, s), 3.98 (1H, dd, J=1.5 and 6 Hz), 4.18–4.34 (1H, m), 5.71 (1H, d, J=1.5 Hz), 7.22 (1H, 2d, J=5.4 Hz), 7.86 (1H, d, J=5.4 Hz)

EXAMPLE 37

4-Nitrobenzyl 5(R)-3-(4-cyanophenoxy)-6(S)-(1(R)-hexanoyloxyethyl)-7-oxo-4-thia-1-azabicyclo[3,2,0]hept-2-ene-2-carboxylate 143 mg of the above compound were obtained from 155 mg of 4-nitrobenzyl 5R-3-(4-cyanophenoxy)-6S-(1R-hydroxyethyl)-7-oxo-4-thia-1-azabicyclo[3,2,0]hept-2-ene-2-carboxylate by a procedure analogous to that described in Example 17 using 0.75 ml of hexanoic anhydride, 5 ml of tetrahydrofuran and 20 mg of 4-dimethylaminopyridine.

$\nu_{max}$: 1795 and 1720 cm$^{-1}$

δ(CDCl₃): 0.87 (3H, m), 1.28 (4H, m), 1.44 (3H, d, J=6.4 Hz), 1.60 (2H, m), 2.29 (2H, m), 3.93 (1H, dd, J=1.5 Hz), 5.20–5.41 (3H, m), 5.69 (1H, d, J=1.5 Hz), 7.22 (2H, d, $J_{AB}$=9 Hz), 7.52 (2H, d, $J_{AB}$=9 Hz), 7.67 (2H, d, $J_{AB}$=8.8 Hz), 8.19 (2H, d, $J_{AB}$=8.8 Hz)

EXAMPLE 38

Potassium 5(R) 3-(4-cyanophenoxy)-6(S)-(1(R)-hexanoyloxyethyl)-7-oxo-4-thia-1-azabicyclo[3,2,0]hept-2-ene-2-carboxylate 87 mg of the above salt were obtained from 127 mg of the corresponding 4-nitrobenzyl carboxylate (see Example 37) by a procedure analogous to that described in Example 11 using 22 mg of potassium bicarbonate and 100 mg of 10% Pd on carbon.

δ(D₂O): 0.90 (3H, m), 1.33 (4H, m), 1.41 (3H, d, J=6.4 Hz), 1.55–2.19 (4H, m), 4.25 (1H, dd, J=1.3 Hz and 5.5 Hz) 5.35 (1H, m) 5.86 (1H, d, J=1.3 Hz) 7.38 (2H, d, $J_{AB}$=8.8 Hz) 7.85 (2H, d, $J_{AB}$=8.8 Hz)

EXAMPLE 39

4-Nitrobenzyl 5(R), 3-(4-cyanophenoxy)-6(S)-(1-(R)-toluoyloxyethyl)-7-oxo-4-thia-1-azabicyclo[3,2,0]hept-2-ene-2-carboxylate 154 mg of the above compound were obtained from 150 mg of 4-nitrobenzyl 5R,3-(4-cyanophenoxy)-6S-(1R-hydroxyethyl)-7-oxo-4-thia-1-azabicyclo[3,2,0]hept-2-ene-2-carboxylate by a procedure analogous to that described in Example 17 using 0.95 g of toluic anhydride, 5 ml of tetrahydrofuran and 20 mg of 4-dimethylaminopyridine.

δ(CDCl₃): 1.56 (3H, d), 2.41 (3H, s), 4.08 (1H, dd, J=1.5 Hz and 7.2 Hz), 5.30 (2H, q), 5.53 (1H, m), 5.83 (1H, d, J=1.5 Hz), 7.18–8.16 (12H, m)

EXAMPLE 40

Potassium 5(R), 3-(4-cyanophenoxy)-6(S)-(1(R)-toluoyloxyethyl)-7-oxo-4-thia-1-azabicyclo[3,2,0]hept-2-ene-2-carboxylate 105 mg of the above salt were obtained from 154 mg of the corresponding 4-nitrobenzyl carboxylate (see Example 39) by a procedure analogous to that described in Example 11, using 26 mg of potassium bicarbonate and 150 mg of 10% Pd on carbon.

δ(D₂O): 1.46 (3H, d, J=6.5 Hz), 2.38 (3H, s), 4.31 (1H, dd, J=1.3 Hz and 5.3 Hz), 5.52 (1H, m), 5.91 (1H, d, J=1.3 Hz), 7.27–7.95 (8H, m)

EXAMPLE 41

4-Nitrobenzyl 5(R),6(S)-(1(R)-(N-benzyloxycarbonylaminoacetoxy)ethyl)-3-(4-cyanophenoxy)-7-oxo-4-thia-1-azabicyclo[3,2,0]hept-2-ene-2-carboxylate 140 mg of the above compound were obtained as an oil from 150 mg of 4-nitrobenzyl 5R,3-(4-cyanophenoxy)-6S-(1R-hydroxyethyl)-7-oxo-4-thia-1-azabicyclo[3,2,0]hept-2-enecarboxylate by a procedure analogous to that described in Example 17 using 900 mg of N-(benzyloxycarbonyl)glycine anhydride, 5 ml of dry THF and 20 mg of 4-dimethylaminopyridine.

δ(CDCl₃): 1.45 (3H, d, J=6.4 Hz), 3.90 (2H, m), 5.10 (2H, s), 5.29 (2H, AB, J=14 Hz), 5.67 (2H, d, J=1 Hz), 7.2–7.4 (7H, m), 7.51 (2H, d, J=8.7 Hz), 7.67 (2H, d, J=9 Hz), 8.19 (2H, s, J=8.8 Hz)

EXAMPLE 42

5(R),6(S)-(1(R)-(aminoacetoxy)ethyl)-3-(4-cyanophenoxy)-7-oxo-4-thia-1-azabicyclo[3,2,0]hept-2-ene-2-carboxylic acid 75 mg of the above amino acid were obtained from 140 mg of the corresponding 4-nitrobenzyl 6-(N-benzyloxycarbonylaminoacetoxyethyl)-3-(4-methylsulphinylphenoxy)-7-oxo-4-thia-1-azabicyclo[3,2,0]hept-2-ene-2-carboxylate (described in Example 41) by a procedure analogous to that described in Example 11, but using no potassium bicarbonate.

EXAMPLE 43

Potassium 5(R),3-(4-ethylsulphinylphenoxy)-6(S)-(1(R)-hydroxyethyl)-7-oxo-4-thia-1-azabicyclo[3,2,0]hept-2-ene-2-carboxylate 39 mg of the above compound were obtained from 54 mg of 4-nitrobenzyl 5(R),3-(4-ethylsulphinylphenoxy)-6(S)-(1(R)-hydroxyethyl)-7-oxo-4-thia-1-azabicyclo[3,2,0]hept-2-ene-2-carboxylate (described in Example 35) by a procedure analogous to that described in Example 11 using 10.4 mg of potassium bicarbonate and 100 mg of 10% palladium on carbon.

δ(D₂O): 1.14 (3H, t J=7.3 Hz), 1.29 (3H, d J=6.4 Hz), 3.0–3.1 (2H, m), 3.95 (1H, dd J=1.0 and 6.2 Hz), 4.32 (1H, m), 5.71 (1H, d J=1.0 Hz), 7.42 and 7.70 (4H, AB J=9 Hz)

EXAMPLE 44

4-Nitrobenzyl 5(R),6(S)-(1(R)-hexanoyloxyethyl)-3(4-methylsulphinylphenoxy)-7-oxo-4-thia-1-azabicyclo[3,2,0]hept-2-ene-2-carboxylate 104 mg of the above compound were obtained as an oil from 150 mg of 4-nitrobenzyl 5(R),6(S)-(1(R)-hydroxyethyl)-3-(4-methylsulphinylphenoxy)-7-oxo-4-thia-1-azabicyclo[3,2,0]hept-2-ene-2-carboxylate by a procedure analogous to that described in Example 9, using 347 μl of hexanoic anhydride, 5 ml of dichloromethane, and 18.3 mg of 4-dimethylaminopyridine.

$\nu_{max}$(CDCl₃): 1795, 1740 (sh) and 1720 cm$^{-1}$

δ(CDCl₃): 0.84–0.89 (3H, m Hz), 1.23–1.29 (4H, m), 1.42 (3H, d J=6.4 Hz), 1.53–1.65 (2H, m), 2.25–2.32 (2H, m), 3.93(1H, dd J=1.4 and 7.5 Hz), 5.25 (1H, d J=14 Hz), 5.27–5.35 (1H, m), 5.43 (1H, d J=14 Hz), 5.67 (1H, J=1.4 Hz), 7.32 (2H, d J=9 Hz), 7.56 (2H, d J=8.7 Hz), 7.68 (2H, d J=8.7 Hz), 8.19 (2H, d J=8.8 Hz)

EXAMPLE 45

Potassium 5(R),6(S)-(1(R)-hexanoyloxyethyl)-3-(4-methylsulphinylphenoxy)-7-oxo-4-thia-1-azabicyclo[3,2,0]hept-2-ene-2-carboxylate 65 mg of the above salt were obtained from 100 mg of the corresponding 4-nitrobenzyl carboxylate (as defined in Example 44) by a procedure analogous to that described in Example 11, using 16.6 mg of potassium bicarbonate and 100 mg of 10% palladium on charcoal.

$\delta(D_2O)$: 0.83 (3H, t J=6.5 Hz), 1.23–1.28 (4H, m), 1.34 (3H, d J=6.5 Hz), 1.53–1.64 (2H, m), 2.38 (2H, t J=7 Hz), 2.86 (3H, s), 4.18 (1H, dd J=1.0 and 5.2 Hz), 5.26–5.31 (1H, m), 5.78 (1H, d J=1.0 Hz), 7.41, 7.75 (4H, AB, J=8.7 Hz)

EXAMPLE 46

2-Cyanothien-3-yl chlorothionoformate 17.7 g of the above compound were obtained as an oil by a procedure analogous to that described in Example 3 using 14.23 g of 2-cyano-3-hydroxythiophene, 17 ml of thiophosgene and 4.55 g of sodium hydroxide.

NMR $\delta(CDCl_3)$: 7.04 (1H, d, J=5.5 Hz), 7.64 (1H, d, J=5.5 Hz)

EXAMPLE 47

4-Nitrobenzyl 3-(2-cyanothien-3-yloxy)-2-(3(S)-[1(R)-dimethyl-(2-methylprop-2-yl)silyl-oxyethyl]-4(R)-ethylthioazetidin-2-on-1-yl)-3-trimethylacetylthio-propenoate 4.1 g of the above compound were obtained by a procedure analogous to that described in Example 36 using 5 g of the azetidinone starting material defined in Example 4, 3.25 g of 2-cyanothien-3-yl chlorothionoformate, 6.5 ml of hexamethyl-disilazane and 18.2 ml of n-butyllithium, and 5 ml of trimethylacetyl bromide.

$\nu_{max}(CDCl_3)$: 1775 and 1735 cm$^{-1}$

NMR of $\delta(CDCl_3)$: 0.04, 0.05 (6H, 2s), 0.80, 0.86 (9H, 2s), 1.09, 1.18 (9H, 2s), 1.26 (6H, m), 2.70 (2H, m), 3.21 (1H, m), 4.25 (1H, m), 5.20–5.42 (3H, m), 6.86–8.25 (6H, m)

EXAMPLE 48

4-Nitrobenzyl 3-(2-cyanothien-3-yloxy)-2-[3(S)-(1(R)-hydroxyethyl)-4(R)-ethylthio-azetidin-2-on-1-yl]-3-trimethyl acetylthio-propenoate 1.41 g of the above compound were obtained from 4.1 g of the corresponding 1(R)-dimethyl-(2-methyl-prop-2-yl)siloxyethyl compound (see Example 47) by a procedure analogous to that described in Example 5, using 4.1 ml of water and 4.1 ml of concentrated hydrocloric acid.

$\nu_{max}(film)$: 1770 and 1735 cm$^{-1}$

NMR $\delta(CDCl_3)$: 1.14, 1.20 (9H, 2s), 1.28 (6H, m), 1.62 (1H, broad), 2.73 (2H, m), 3.29 (1H, m), 4.25 (1H, m), 5.33 (3H, bs), 6.82–7.46 (2H, m), 7.48–8.25 (4H, m)

EXAMPLE 49

4-Nitrobenzyl 3-(2-cyanothien-3-yloxy)-2-[3(S)-{1(R)-hydroxyethyl}-4(S)-chloro-azetidin-2-on-1-yl)-3-trimethylacetylthiopropenoate 1.67 g of the above compound were obtained by a process analogous to that described in Example 6 using 2.31 g of the 1(R)-hydroxyethylazetidinone derivative defined in Example 48 and a solution of 4.1 mmol of chlorine in 5.2 ml of carbon tetrachloride. The product is isolated as a mixture of E and Z isomers, observed as double peaks in the nmr spectrum.

$\nu_{max}(film)$: 1785 and 1735 cm$^{-1}$

NMR $\delta(CDCl_3)$: 1.10, 1.16 (9H, 2s), 1.41, 1.46 (3H, 2d, J=6 Hz), 1.60 (1H, s), 3.58 (1H, 2dd), 4.38 (1H, m), 5.33, 5.35 (2H, 2s), 6.14, 6.19 (1H, 2d, J=4.3 Hz), 6.86–8.26 (6H, m)

EXAMPLE 50

4-Nitrobenzyl 5(R),6(S)-(1(R)-hydroxyethyl)-3-(2-cyanothien-3-yloxy)-7-oxo-4-thia-1-azabicyclo[3,2,0]hept-2-ene-2-carboxylate 114 mg of the above compound were obtained by a procedure analogous to that described in Example 7 using 275 mg of the product of Example 49 and 70 mg of imidazole. $\nu_{max}(film)$: 1790 and 1715 cm$^{-1}$ $\delta(CDCl_3)$: 1.38 (3H, d, J=6.4 Hz), 1.59 (1H, broad), 3.87 (1H, dd, J=1.5 Hz and 6.6 Hz), 4.29 (1H, m), 5.33 (2H, q), 5.76 (1H, d, J=1.5 Hz), 6.93 (1H, d, J=5.5 Hz), 7.53 (3H, m), 8.21 (2H, d $J_{AB}$=8.8 Hz)

EXAMPLE 51

4-Nitrobenzyl 5(R),3-(2-cyanothien-3-yloxy)-6(S)-{1(R)-ethoxy acetoxyethyl}-7-oxo-4-thia-1-azabicyclo[3,2,0]hept-2-ene-2-carboxylate 3 mg of the above compound were obtained from 5 mg of the corresponding 1(R)-hydroxy compound (defined in Example 50) by a procedure analogous to that described in Example 17 using 20 mg of ethoxyacetic anhydride, 2 ml of dichloromethane and 0.5 mg of dimethylaminopyridine.

$\delta(CDCl_3)$: 1.25 (3H, m), 1.51 (3H, d, J=6.4 Hz), 3.63 (2H, m), 4.03 (1H, dd, J=1.5 Hz and 6.4 Hz), 4.10 (2H, s), 5.24–5.44 (3H, m), 5.74 (1H, d, J=1.5 Hz), 6.93–8.26 (6H, m)

EXAMPLE 52

4-Nitrobenzyl 5(R),3-(2-cyanothien-3-yloxy)-6(S)-(1(R)-phenylacetoxyethyl)-7-oxo-4-thia-1-azabicyclo[3,2,0]hept-2-ene-carboxylate 3.5 mg of the above compound were obtained from 5 mg of the corresponding 1(R)-hydroxy compound (see Example 50) by a procedure analogous to that described in Example 17, using 25 mg of phenylacetic anhydride, 2 ml of dichloromethane and 0.5 mg of dimethylaminopyridine.

$\delta(CDCl_3)$: 1.41 (3H, d, J=6.5 Hz), 3.61 (2H, m), 3.94 (1H, dd, J=1.6 Hz and 7.7 Hz), 5.22–5.43 (3H, m), 5.55 (1H, d, J=1.6 Hz), 6.89 (1H, d, J=5 Hz), 7.51 (3H, m), 8.20 (2H, d, $J_{AB}$=8.8 Hz)

EXAMPLE 53

Potassium 5(R),3-(2-cyanothien-3-yloxy)-6(S)-(1(R)-{phenylacetoxy}ethyl)-7-oxo-4-thia-1-aza-bicyclo[3,2,0]hept-2-ene-2-carboxylate 2.5 mg of the above compound were obtained from 3.3 mg of the corresponding 4-nitrobenzyl carboxylate (defined in Example 52) by a procedure analogous to that described in Example 11, using 0.4 mg of potassium bicarbonate.

$\delta(D_2O)$: 1.38 (3H, d J=6.5 Hz), 3.60 (2H, s), 4.08 (1H, dd J=1.6 Hz and 7.7 Hz), 5.30 (1H, m), 5.85 (1H, d J=1.6 Hz), 7.10 (1H, d J=5 Hz), 7.87 (1H, d J=5 Hz)

EXAMPLE 54

4-Nitrobenzyl 5(R),3-(2-cyanothien-3-yloxy)-6(S)-(1(R)-trifluoroacetoxyethyl)-7-oxo-4-thia-1-azabicyclo[3,2,0]hept-2-ene-2-carboxylate 2.9 mg of the above compound were obtained from 5 mg of the corresponding 1(R)-hydroxy compound (see Example 50) by a procedure analogous to that described in Example 17, using 15 μl of trifluoroacetic anhydride, 2 ml of dichloromethane and 0.5 mg of dimethylaminopyridine.

$\delta(CDCl_3)$: 1.58 (3H, d, J=6.4 Hz), 4.11 (1H, dd, J=1.5 Hz and 7 Hz), 5.28–5.45 (3H, m), 5.74 (1H, d, J=1.5 Hz), 6.93 (1H, d, J=5.6 Hz), 7.28–8.23 (5H, m)

EXAMPLE 55

4-Nitrobenzyl 5(R),6(S)-(1(R)-(4-chlorobenzoyl)oxyethyl)-3-(2-cyanothien-3-yloxy)-7-oxo-4-thia-1-azabicyclo[3,2,0]hept-2-ene-2-carboxylate 3.1 mg of the above compound were obtained from 5 mg of the corresponding 1(R)-hydroxy compound (see Example 50) by a procedure analogous to that described in Example 17, using 30 mg of 4-chlorobenzoic anhydride, 5 ml of dichloromethane and 0.5 mg of dimethylaminopyridine.

$\delta(CDCl_3)$: 1.55 (3H, d, J=6.4 Hz), 4.12 (1H, dd, J=1.5 Hz and 6.8 Hz), 5.26, 5.40 (2H, AB, J=14 Hz), 5.5 (1H, m), 5.86 (1H, d, J=1.5 Hz), 6.93 (1H, d, J=5.5 Hz), 7.33–8.20 (9H, m)

EXAMPLE 56

4-Nitrobenzyl 5(R),3-(2-cyanothien-3-yloxy)-6(S)-1(R)-cyclopentylacetoxyethyl)-7-oxo-4-thia-1-azabicyclo[3,2,0]hept-2-ene-2-carboxylate 3.4 mg of the above compound were obtained from 5 mg of the corresponding 1(R)-hydroxy compound (see Example 50) by a procedure analogous to that described in Example 17, using 25 mg of cyclopentylacetic anhydride, 2 ml of dichloromethane and 0.5 mg of dimethylaminopyridine.

$\delta(CDCl_3)$: 1.1–2.2 (9H, m), 1.41 (3H, d, J=6.4 Hz), 2.31 (2H, d, J 7 Hz), 3.98 (1H, dd, J=1.6 Hz and 7.3 Hz), 5.24, 5.33 (2H, AB, J=13.7 Hz), 5.30 (1H, m), 5.73 (1H, d, J=1.6 Hz), 6.92 (1H, d, J=5.5 Hz), 7.52 (1H, d, J=5.5 Hz), 7.55 (2H, d, J=8.8 Hz), 8.20 (2H, d, $J_{AB}$=8.8 Hz)

EXAMPLE 57

4-Nitrobenzyl 5(R),3-(2-cyanothien-3-yloxy)-6(S)-(1(R)-cyclopropylcarbonyloxyethyl)-7-oxo-4-thia-1-azabicyclo[3,2,0]hept-2-ene-2-carboxylate 3.2 mg of the above compound were obtained from 5 mg of the corresponding 1(R)-hydroxy compound (see Example 50) by a procedure analogous to that described in Example 17, using 6 mg of cyclopropanecarboxylic anhydride, 2 ml of dichloromethane and 0.5 mg of dimethylaminopyridine.

$\delta(CDCl_3)$: 0.83–1.33 (4H, m), 1.42 (3H, d, J=6 Hz), 1.70 (1H, m), 4.01 (1H, dd, J=1.5 Hz and 7 Hz), 5.24–5.35 (3H, m), 5.73 (1H, d, J=1.5 Hz), 6.93 (1H, d, J=5.5 Hz), 7.55 (3H, m), 8.20 (2H, d, $J_{AB}$=8.8 Hz)

EXAMPLE 58

4-Nitrobenzyl 5(R),6(S)-(1(R)-acetoxyethyl)-3-(2-cyanothien-3-yloxy)-7-oxo-4-thia-1-azabicyclo[3,2,0]hept-2-ene-2-carboxylate 75 mg of the above compound were obtained from 100 mg of the corresponding 1(R)-hydroxy compound (see Example 50) by a procedure analogous to that described in Example 17, using 0.4 ml of acetic anhydride, 10 ml of dichloromethane and 15 mg of dimethylaminopyridine.

$\delta(CDCl_3)$: 1.42 (3H, d, J=6.4 Hz), 2.06 (3H, s), 4.00 (1H, dd, J=1.6 Hz and 7.4 Hz), 5.21–5.45 (3H, m), 5.73 (1H, d, J=1.6 Hz), 6.92 (1H, d, J=5.5 Hz), 7.52 (3H, m), 8.21 (2H, d, $J_{AB}$=8.8 Hz)

EXAMPLE 59

Potassium 5(R),6(S)-(1(R)-acetoxyethyl)-3-(2-cyanothien-3-yloxy)-7-oxo-4-thia-1-azabicyclo[3,2,0]hept-2-ene-2-carboxylate 35 mg of the above salt were obtained from 70 mg of the corresponding 4-nitrobenzyl carboxylate (see Example 58) by a procedure analogous to that described in Example 11, using 13.6 mg of potassium bicarbonate and 70 mg of 10% Pd on carbon.

$\delta(DMSO)$: 1.27 (3H, d, J=6 Hz), 2.02 (3H, s), 4.10 (1H, m), 5.12 (1H, m), 5.71 (1H, d, J=1.3 Hz), 7.10 (1H, d, J=5.5 Hz), 7.96 (1H, d, J=5.5 Hz)

EXAMPLE 60

Potassium 5(R),3-(2-cyanothien-3-yloxy)-6(S)-{1(R)-trifluoroacetoxyethyl}-7-oxo-4-thia-1-azabicyclo[3,2,0]hept-2-ene-2-carboxylate 2 mg of the above compound were obtained from 2.9 mg of the corresponding 4-nitrobenzyl carboxylate (defined in Example 54) by a procedure analogous to that defined in Example 11, using 0.5 mg of potassium bicarbonate and 2 mg of 10% palladium on carbon.

EXAMPLE 61

Potassium 5(R),3-(2-cyanothien-3-yloxy)-6(S)-{1(R)-(2-ethoxyacetoxy)ethyl}-7-oxo-4-thia-1-azabicyclo[3,2,0]hept-2-ene-2-carboxylate 2 mg of the above compound were obtained from 2.9 mg of the corresponding 4-nitrobenzyl carboxylate defined in Example 51) by a procedure analogous to that defined in Example 11, using 0.5 mg of potassium bicarbonate and 2 mg of 10% palladium on carbon.

EXAMPLE 62

4-Nitrobenzyl 5(R),3-(2-cyanothien-3-yloxy)-6(S)-(1(R)-cyclopropylcarbonyloxyethyl)-7-oxo-4-thia-1-aza-bicyclo[3,2,0-]hept-2-ene-2-carboxylate 2.1 mg of the above compound were obtained from 3.1 mg of the corresponding 4-nitrobenzyl carboxylate (defined in Example 57) by a procedure analogous to that described in Example 11, using 0.4 mg of potassium bicarbonate.

$\delta(D_2O)$: 0.79–1.35 (4H, m), 1.38 (3H, d J=6 Hz), 1.70 (1H, m), 4.21 (1H, dd J=1.5 Hz and 7 Hz), 5.30 (1H, m), 5.85 (1H, d J=1.5 Hz), 7.18 (1H, d J=5.5 Hz), 7.85 (1H, d J=5.5 Hz)

EXAMPLE 63

Potassium 5(R),3-(2-cyanothien-3-yloxy)-6(S)-(1(R)-{cyclopentylacetoxy}ethyl)-7-oxo-4-thia-1-aza-bicyclo[3,2,0-]hept-2-ene-2-carboxylate 2.5 mg of the above compound were obtained from 3.3 mg of the corresponding 4-nitrobenzyl carboxylate (defined in Example 56) by a procedure analogous to that described in Example 11, using 0.4 mg of potassium bicarbonate.

$\delta(D_2O)$: 1.1–2.2 (9H, m), 1.41 (3H, d J=6.4 Hz), 2.30 (2H, m), 4.11 (1H, dd J=1.6 Hz and 7.3 Hz), 5.30 (1H, m), 5.85 (1H, d J=1.6 Hz), 7.18 (1H, d J=5.5 Hz), 7.85 (1H, d J=5.5 Hz)

EXAMPLE 64

Potassium 5(R),3-(2-cyanothien-3-yloxy)-6(S)-(1(R)-{4-chlorobenzoyloxy}ethyl)-7-oxo-4-thia-1-aza-bicyclo[3,2,0]-hept-2-ene-2-carboxylate 2.5 mg of the above compound were obtained from 3.0 mg of the corresponding 4-nitrobenzyl carboxylate (defined in Example 55) by a procedure analogous to that described in Example 11, using 0.4 mg of potassium bicarbonate.

$\delta(D_2O)$: 1.42 (3H, d J=6 Hz), 4.22 (1H, dd J=1.5 Hz and 7 Hz), 5.5 (1H, m), 5.89 (1H, d J=1.5 Hz), 7.15 (1H, d J=5.5 Hz), 7.40 (2H, d J=9 Hz), 7.75 (2H, d J=9 Hz), 7.85 (1H, d J=5.5 Hz)

EXAMPLE 65

Potassium 5(R),6(S)-(1(R)-hydroxyethyl)-3-(2-cyanothien-3-yloxy)-7-oxo-4-thia-1-azabicyclo[3,2,0]hept-2-ene-2-carboxylate 206 mg of the above salt were obtained from 300 mg of the corresponding 4-nitrobenzyl carboxylate (see Example 50) by a procedure analogous to that described in Example 11 using 63.4 mg of potassium bicarbonate and 300 mg of 10% Pd on carbon.

$\delta(D_2O)$: 1.27 (3H, d, J=6.4 Hz), 3.98 (1H, dd, J=1.2 Hz and 7.2 Hz), 4.24 (1H, m), 5.74 (1H, d, J=1.2 Hz), 7.04 (1H, d, J=5.5 Hz), 7.75 (1H, d, J=5.5 Hz)

EXAMPLE 66

4-Nitrobenzyl 5(R)-3-(4-ethylsulphinylphenoxy)-6(S)-{1(R)-hexanoyloxyethyl}-7-oxo-4-thia-1-azabicyclo[3,2,0]hept-2-ene-2-carboxylate 123 mg of the above compound were obtained from 178 mg of the corresponding 1(R)-hydroxyethyl compound (defined in Example 35) by a procedure analogous to that described in Example 17, using 630 µl of hexanoic anhydride, 8 ml of dichloromethane and 25 mg of dimethylaminopyridine.

$\delta(CDCl_3)$: 0.83–0.92 (3H, m), 1.12–1.25 (4H, m), 1.42 (3H, d J=6.4 Hz), 1.56–1.67 (2H, m), 2.76, 2.91 (2H, ABq J=7.5 and $J_{AB}$=14.8 Hz), 3.90 (1H, dd J=1.4 and 7.7 Hz), 5.24, 5.42 (2H, AB J=13.7 Hz), 5.26–5.31 (1H, m), 7.30 (2H, d J=8.8 Hz), 7.56 (2H, d J=8.7 Hz), 7.63 (2H, d J=8.7 Hz), 8.20 (2H, d J=8.7 Hz)

EXAMPLE 67

Potassium 5(R)-3-(4-ethylsulphinylphenoxy)-6(S)-{1(R)-hexanoyloxyethyl}-7-oxo-4-thia-1-aza-bicyclo[3,2,0]hept-2-ene-2-carboxylate 49 mg of the above salt were obtained from 123 mg of 4-nitrobenzyl 5(R)-3-(4-ethylsulphinylphenoxy)-6(S)-{1(R)-hexanoyloxyethyl}-7-oxo-4-thia-1-azabicyclo[3,2,0]-hept-2-ene-2-carboxylate by a procedure analogous to that described in Example 11, using 20 mg of potassium bicarbonate and 10 mg of 10% palladium on carbon.

EXAMPLE 68

4-Nitrobenzyl 5(R),6(S)-(1R-hexanoyloxyethyl)-3-(4-methylsulphonylphenoxy)-7-oxo-4-thia-1-azabicyclo[3,2,0]hept-2-ene-2-carboxylate 93 mg of the above compound were obtained as an oil from 130 mg of 4-nitrobenzyl 5R,6S-(1R-hydroxyethyl)-3-(4-methylsulphinylphenoxy)-7-oxo-4-thia-1-azabicyclo[3,2,0]hept-2-ene-2-carboxylate by a procedure analogous to that described in Example 17 and using 347 µl of hexanoic anhydride, 5 ml of dichloromethane, and 18 mg of 4-dimethylaminopyridine.

$\delta(CDCl_3)$: 0.87 (3H, t J=6.7 Hz), 1.22–1.33 (4H, m), 1.43 (3H, d J=6.4 Hz), 1.54–1.66 (2H, m), 2.30 (2H, t J=7.4 Hz), 3.08 (3H, s), 3.98 (1H, dd J=1.5 and 7.4 Hz), 5.23 (1H, d J=14 Hz), 5.26–5.37 (1H, m), 5.40 (1H, d J=14 Hz), 5.73 (1H, d J=1.5 Hz), 7.31 (2H, d J=8.5 Hz), 7.53 (2H, d J=8.5 Hz), 7.97 (2H, d J=8.5 Hz), 8.19 (2H, d J=8.5 Hz)

EXAMPLE 69

Potassium 5(R),6(S)-(1(R)-hexanoyloxyethyl)-3-(4-methylsulphonylphenoxy)-7-oxo-4-thia-1-azabicyclo[3,2,0]hept-2-ene-2-carboxylate 27 mg of the above salt were obtained from 75 mg of the corresponding 4-nitrobenzyl carboxylate (defined in Example 68) by a procedure analogous to that described in Example 11 using 11 mg of potassium bicarbonate and 100 mg of 10% palladium on carbon.

$\delta(D_2O)$: 0.85 (3H, t J=6.7 Hz), 1.22–1.32 (4H, m), 1.35 (3H, d J=6.5 Hz), 1.43–1.65 (2H, m), 2.39 (2H, t J=7.2 Hz), 3.24 (3H, s), 4.22 (1H, dd J=1.5 and 5.3 Hz), 5.26–5.35 (1H, m), 5.82 (1H, d J=1.5 Hz), 7.42, 7.97 (4H, AB J=8.9 Hz).

We claim:

1. A compound of the formula I

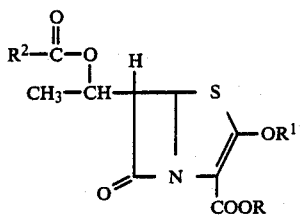

in which

R represents a hydrogen atom or a carboxyl esterifying group, removable by hydrolysis, by photolysis, by reduction or by enzyme action to give the free acid;

$R^1$ represents a phenyl, naphthyl or thienyl group bonded at a ring carbon atom to the oxygen atom attached to the 2-position of the penem ring structure, a group $R^1$ being unsubstituted or substituted by one, two or three substituents, which may be the same or different, selected from halogen atoms and —OH, —NH$_2$, —NO$_2$, —CN, —N$_3$, $R^3$—, $R^3$O—, $R^3$S—, $R^3$—SO—, $R^3$—SO$_2$, $R^3$—CO—, $R^3$O—CO—, $R^3$—CO—O—, H$_2$N—CO—,

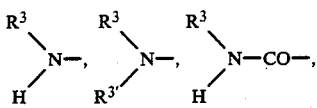

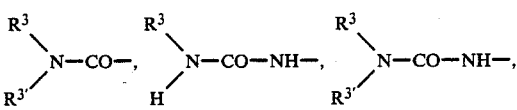

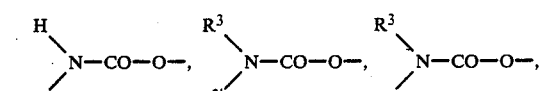

$R^3$—CO—NH—, NH$_2$—CO—NH—, $R^3$—SO$_2$—NH—, NH$_2$—SO$_2$—NH—, H$_2$N—SO$_2$—,

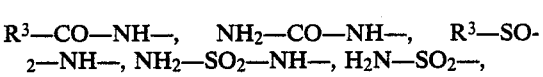

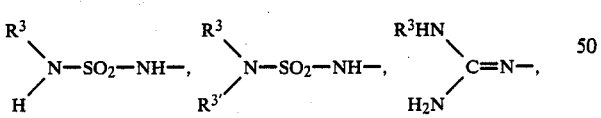

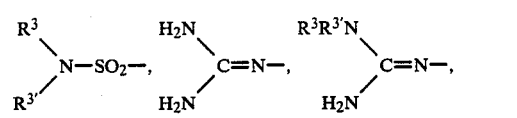

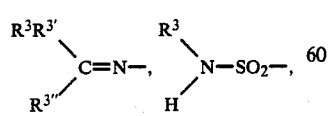

—CF$_3$, —SCF$_3$, —SOCF$_3$, —SO$_2$CF$_3$ and HO—CO groups, in which $R^3$, $R^{3'}$ and $R^{3''}$ each represents an alkyl group having from 1 to 4 carbon atoms, $R^3$, $R^{3'}$ and $R^{3''}$ being the same or different, but as substituent on $R^1$ not more than one should be selected from (a) —OH and —NH$_2$ groups and not more than one should be selected from (b) —CN, —NO$_2$, $R^3$—CO—, $R^3$O—CO—, $R^3$—SO— and $R^3$—SO$_2$—groups, $R^2$ represents (ii) a straight or branched chain alkyl group having from 1 to 5 carbon atoms, which is substituted by one or more substituents, which may be the same or different, selected from the following:

(a) alkenyl and alkynyl groups having up to 4 carbon atoms;

(b) cycloalkyl and cycloalkenyl groups having from 3 to 7 carbon atoms;

(c) phenyl groups, which may be unsubstituted or substituted by one or more substituents, which may be the same or different, selected from alkyl, alkylthio or alkoxy groups having up to 4 carbon atoms; halogen atoms, trifluormethyl groups; cyano groups; carboxyl groups; groups of the formula —COOR$^4$ in which R$^4$ represents an alkyl group having up to 4 carbon atoms; amido and sulphonamido groups; groups of the formula

in which $R^5$ and $R^6$, which may be the same or different, each represents a hydrogen atom or a group —COR$^4$, —SO$_2$R$^4$, or R$^4$, in which R$^4$ is defined as above;

(d) trifluormethyl and 2,2,2-trifluorethyl groups;

(e) halogen atoms;

(f) hydroxy groups, alkoxy groups having up to 4 carbon atoms, and phenoxy groups, in which the phenyl moiety is substituted as defined in (c) above, acyloxy groups of the formula R$_a^2$CO$_2$ and acyl groups of the formula R$_a^2$CO—, in which R$_a^2$ is a straight or branched chain alkyl group having from 1 to 5 carbon atoms, which is unsubstituted or substituted by one or more substituents, which may be the same or different, selected from the following:

(1) phenyl, (2) halogen atoms, hydroxy groups, or groups of the formula

where $R^5$ and $R^6$ are as defined in (c) above;

(g) cyano and azido groups; and (h) amino groups and groups of the formula

in which $R^5$ and $R^6$ are as defined in (c) above; or (iii) $R^2$ represents a cycloalkyl group which has from 3 to 7 carbon atoms and which may be unsubstituted or substituted as defined above for an alkyl group $R^2$; or (iv) $R^2$ represents a phenyl group which is substituted as defined in (c) above.

2. A compound as claimed in claim 1, wherein $R^1$ represents an unsubstituted phenyl group or a phenyl group substituted by a chlorine, fluorine, trifluoromethyl, methyl, methoxy, nitro, cyano, amino, methylthio, methylcarbonylamino, methylsulphonylamino or methylaminocarbonylamino group, or a phenyl group substituted by two or three methyl or methoxy groups, or a heterocyclic group having one or two methyl substituents.

3. A compound as claimed in claim 1, wherein $R^1$ represents presents a phenyl group substituted by a hydroxy, acetoxy, methylsulphinyl or methylsulphonyl group.

4. A compound as claimed in claim 1, wherein a carboxyl esterifying group R is removable by hydrolysis, by photolysis, by reduction or by enzyme action to give the free acid, or by any two or more of such methods.

5. a compound as claimed in claim 1, wherein R represents a p-nitrobenzyl, phthalidyl, pivaloyloxymethyl, acetylmethyl or acetoxymethyl group.

6. A compound as claimed in claim 1, wherein a carboxyl esterifying group R is physiologically cleavable.

7. A compound as claimed in claim 1, wherein $R^1$ represents a phenyl or thienyl group, being unsubstituted or substituted as defined in claim 1.

8. A compound as claimed in claim 7, wherein a group $R^1$ is substituted by $(C_1-C_4)$-alkylsulphinyl, $(C_1-C_4)$-alkylsulphenyl, nitrile and/or halogen.

9. A compound as claimed in claim 7, wherein a group $R^1$ is substituted by fluorine.

10. A compound as claimed in claim 7, wherein $R^2$ represents $(C_1-C_5)$-alkyl, $(C_3-C_7)$-cycloalkyl, hydrogen or a kation of a physiologically tolerable base.

11. A physiologically tolerable salt of a compound of formula I as claimed in any one of claims 2, 3, or 1 in which R represents a hydrogen atom.

12. A pharamaceutical preparation which comprises a compound of formula I as claimed in claim 1 or a physiologically tolerable salt thereof or a mixture of two or more of such substances as active ingredient, in admixture or conjunction with a pharmaceutically suitable carrier.

13. A compound of formula I as claimed in claim 1 or a physiologically tolerable salt thereof, for use as a β-lactam inhibitor and/or as an antibacterial agent.

* * * * *